US006323000B2

(12) United States Patent
Briggs et al.

(10) Patent No.: US 6,323,000 B2
(45) Date of Patent: *Nov. 27, 2001

(54) VARIANT HUMAN α7 ACETYLCHOLINE RECEPTOR SUBUNIT, AND METHODS OF PRODUCTION AND USES THEREOF

(76) Inventors: Clark A. Briggs, 2280 Shannondale, Libertyville, IL (US) 60048; Murali Gopalakrishnan, 1568 Oxford Cir., Grayslake, IL (US) 60030; David G. McKenna, 3404 Cove Ct., McHenry, IL (US) 60050; Lisa M. Monteggia, 239 Dittmer, Apt. 2A, Lindenhurst, IL (US) 60046; Jean-Marc Roch, 1020 Lakehurst Dr., Apt. 109, Waukegan, IL (US) 60085; James P. Sullivan, 705 Dimmeydale Dr., Deerfield, IL (US) 60015; Edward Touma, 3313 Beacon St. #204, North Chicago, IL (US) 60064

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/771,737

(22) Filed: Dec. 20, 1996

(51) Int. Cl.[7] .......................... C12P 21/02; C07H 21/02; C07H 21/04; C12N 15/63
(52) U.S. Cl. .................. 435/69.1; 435/71.1; 435/254.2; 435/320.1; 435/325; 536/23.5
(58) Field of Search .......................... 536/23.5; 435/69.1, 435/320.1, 325, 254.2, 71.1

(56) References Cited

U.S. PATENT DOCUMENTS 5,202,257 * 4/1993 Heinemann et al. .

FOREIGN PATENT DOCUMENTS 9420617   9/1994  (WO) .

OTHER PUBLICATIONS

Sequela et al *J Neuroscience* 13(2) 597–604 (1993).*
Sambrook et al "Molecular Cloning: A Laboratory Manual" 2nd Edition (1989) Cold Spring Harbor Press, USA, pp 16.2–16.4.*
Elliott, K.J. et al. "Comparative structure of human neuronal alpha 2–alpha 7 and β2–β4 nicotinic acetylcholine receptor subunits and functional expression of the alpha 2, alpha 3, alpha 4, alpha 7, β2, and β4 subunits" Journal of Molecular Neuroscience, vol. 7, 1996, pp 217–228.
Galzi, J.–L. and Changeux, J.–P. "Review: Neurotransmitter Receptors VI; Neuronal nicotinic receptors: molecular organization and regulations" Neuropharmacology, vol. 34, No. 6, 1995, pp 563–582.

Peng, X. et al. "Human alpha 7 acetylcholine receptor: Cloning of the alpha 7 subunit from the SH–SY5Y cell line and determination of pharmacological properties of native receptors and functional alpha 7 homomers expressed in Xenopus oocytes" Molecular Pharmacology, vol. 45, No. 3, Mar. 1994, pp. 546–554.
L. E. Adler et al., *Biol. Psychiartry*, vol. 32, 607–616 (1992).
M. H. Akabas et al., *Biochem.*, vol. 34, 12496–12500 (1995).
A. Akaike et al., *Brain Res.*, vol. 644, 181–187 (1994).
K. Aoshiba et al., *J. Lab. Clin. Med.*, vol. 127, 186–194 (1996).
M. Ballivet et al., *J. Mol. Biol.*, vol. 258, 261–269 (1996).
C. Beck et al., *Neurobiol. Disease*, vol. 1 95–99 (1994).
C. Beck et al., *Epilepsia*, vol. 36, S28 (1995).
D. Bertrand et al., *Proc. Natl. Acad. Sci. (USA)*, vol. 89, 1261–1265 (1992).
D. Bertrand et al., *Pro. Natl. Acad. Sci. (USA)*, vol. 90, 6971–6975 (1993).
D. Bertrand et al., *Sem. Neurosci.*, vol. 7, 75–90 (1995).
R. Blitzer et al., *Neurosci. Lett.*, vol. 119, 207–210 (1990).
J.–P. Changeux et al., *Trends Pharmacol. Sci.*, vol. 13, 299–301 (1992a).
J.–P. Changeux et al., *Q. Rev. Biophys.*, vol. 25, 395–432 (1992b).
J. Chen et al., *Biophys. J.*, vol. 69, 849–859 (1995).
S. Couturier et al., *Neuron.*, vol. 5, 847–856 (1990).
D. Donnelly–Roberts et al., *Brain Res.*, vol. 719, 36–44 (1996).
A. Engel et al., *Ann. Neurol.*, vol. 40, 810–817 (1996).
A. Ferrer–Montiel et al., *FEBS Lett.*, vol. 324, 185–190 (1993).
G. Filatov et al., *Mol. Pharmacol.*, vol. 48, 379–384 (1995).
R. Freedman et al., *J. Neurosci.*, vol. 13, 1965–1975 (1993).
R. Freedman et al., *Proc. Natl. Acad. Sci. (USA)*, vol. 94, 587–592 (1997).
J. Freeman et al., *Nature*, vol. 269, 218–222 (1977).
K. Fuxe et al., *Clin. Investig.*, vol. 72, 262–268 (1994).
J.–L. Galzi et al., *FEBS Lett.*, vol, 294, 198–202 (1991).
J.–L. Galzi et al., *Nature*, vol. 359, 500–505 (1992).
M. Garcia–Guzman et al., *Eur. J. Neurosci.*, vol. 7, 647–655 (1995).
M. Gopalakrishnan et al., *Eur. J. Pharmacol. –Mol. Pharmacol.*, vol. 290, 237–246 (1995).
F. Hory–Lee et al., *J. Neurosci.*, vol. 15, 6453–6460 (1995).

(List continued on next page.)

Primary Examiner—Gary L. Kunz
Assistant Examiner—Stephen Gucker
(74) Attorney, Agent, or Firm—Mimi C. Goller

(57) ABSTRACT

A variant human α7 nicotinic acetylcholine receptor (nAChR) polypeptide is provided wherein the variant contains an amino acid substitution at the valine–274 position of the wild-type human α7 nAChR. Nucleic acid molecules encoding the variant human α7 nAChR, receptors and host cells containing such nucleic acid molecules are also provided. In addition, methods are provided for producing the variant as are methods of using such variants for screening compounds for activity at the nAChR.

20 Claims, 10 Drawing Sheets

OTHER PUBLICATIONS

B. Hunter et al., *Neurosci. Lett.*, vol. 168, 130–134 (1994).
K. Imoto et al., *Nature*, vol. 335, 645–648 (1988).
J. James et al., *Behav. Genet.*, vol. 25, 149–159 (1995).
A. Janson et al., *Neurosci.*, vol. 57, 931–941 (1993).
P. Kienker et al., *Biophys. J.*, vol. 66, 325–334 (1994).
R. Krause et al., *J. Physiol.* (*London*), vol. 489, 779–790 (1995).
S. Leonard et al., *Schizophr. Bull.*, vol. 22, 431–445 (1996).
V. Luntz–Leybman et al., *Brain Res.*, vol. 587, 130–136 (1992).
P. Marin et al., *NeuroReport*, vol. 5, 1977–1980 (1994).
E. Martin et al., *Drug. Dev. Res.*, vol. 31, 135–141 (1994).
C. Newland et al., *J. Physiol.* (*London*), vol. 487P, P 208 (1995a).
C. Newland et al., *J. Physiol.* (*London*), vol. 489, 767–778 (1995b).
A. Owen et al., *NeuroReport*, vol. 6, 2269–2272 (1995).
P. Pugh et al., *J. Neurosci.*, vol. 14, 889–896 (1994).
M. Quik et al., *Brain Res.*, vol. 655, 161–167 (1994).
F. Revah et al., *Nature*, vol. 353, 846–849 (1991).
I. Rinner et al., *Biochem. Biophys. Res. Commun.*, vol. 203, 1057–1062 (1994).
S. Sawada et al., *Neurosci. Res.*, vol. 20, 317–322 (1994a).
S. Sawada et al., *Neurosci. Res.*, vol. 20, 323–329 (1994b).
S. Sine et al., *Neuron*, vol. 15, 205–211 (1995).
O. Steinlein et al., *Nature Genetics*, vol. 11, 201–203 (1995).
O. Steinlein et al., *Am. J. Med. Genet.*, vol. 74, 199–201 (1997).
K. Stevens et al., *Neuropsychopharmacol.*, vol. 15, 152–162 (1996).
J. Sullivan et al., *Soc. Neurosci. Abstr.*, vol. 22, 1263 (1996).
S. Tamamizu et al., *Cell. Mol. Neurobiol.*, vol. 15, 427–438 (1995).
M. Treinin et al., *C. elegans. Neuron*, vol. 14, 71–877 (1995).
A. Villarroel et al., *Proc. R. Soc. Lond.* [*Biol.*], vol. 243, 69–74 (1991).
M. Wayner et al., *Peptides*, vol. 17, 1127–1133 (1996).

\* cited by examiner

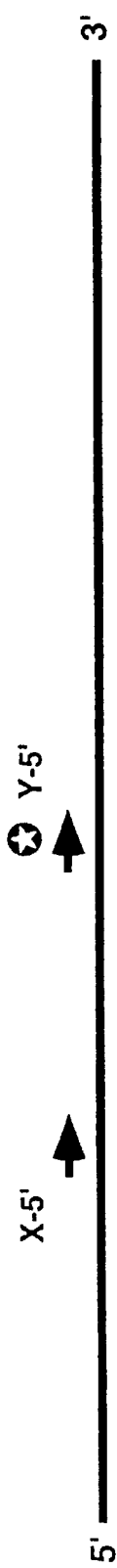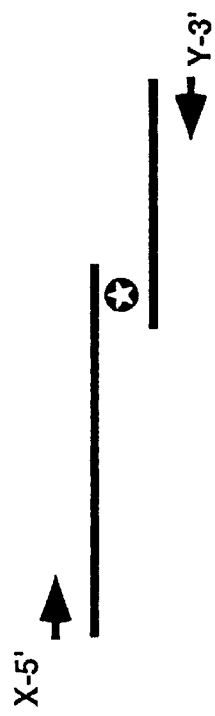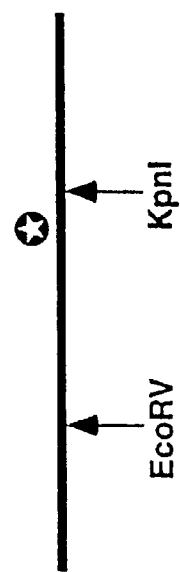

```
TCGAGCCC ATG AGG TGT AGC CCC GGA GTG TGG CTG GCA CTG GCA          39
         M   R   C   S   P   G   V   W   L   A   L   A           13

GCA TCT CTC CTG CAC GTG TCC CTG CAA GGC GAG TTC CAG AGG AAG CTT   87
 A   S   L   L   H   V   S   L   Q   G   E   F   Q   R   K   L   29

TAC AAG GAG CTG GTC AAG AAC TAC AAT CCC TTG GAG AGG CCC GTG GCC  135
 Y   K   E   L   V   K   N   Y   N   P   L   E   R   P   V   A   45

AAT GAC TCG CAA CCA CTC ACC GTC TAC TTC TCC CTG AGC CTC CTG CAG  183
 N   D   S   Q   P   L   T   V   Y   F   S   L   S   L   L   Q   61

ATC ATG GAC GTG GAT GAG AAG AAC CAA GTT TTA ACC ACC AAC ATT TGG  231
 I   M   D   V   D   E   K   N   Q   V   L   T   T   N   I   W   77

CTG CAA ATG TCT TGG ACA GAT CAC TAT TTA CAG TGG AAT GTG TCA GAA  279
 L   Q   M   S   W   T   D   H   Y   L   Q   W   N   V   S   E   93

TAT CCA GGG GTG AAG ACT GTT CGT TTC CCA GAT GGC CAG ATT TGG AAA  327
 Y   P   G   V   K   T   V   R   F   P   D   G   Q   I   W   K   109

CCA GAC ATT CTT CTC TAT AAC AGT GCT GAT GAG CGC TTT GAC GCC ACA  375
 P   D   I   L   L   Y   N   S   A   D   E   R   F   D   A   T   125
```

FIG. 2A

| | | | | | | | | | | | | | | | |
|---|---|---|---|---|---|---|---|---|---|---|---|---|---|---|---|
|TTC|CAC|ACT|AAC|GTG|TTG|GTG|AAT|TCT|TCT|GGG|CAT|TGC|CAG|TAC|CTG|
|F|H|T|N|V|L|V|N|S|S|G|H|C|Q|Y|L|
| | | | | | | | | | | | | | |423|
| | | | | | | | | | | | | | |141|
|CCT|CCA|GGC|ATA|TTC|AAG|AGT|TCC|TGC|TAC|ATC|GAT|GTA|CGC|TGG|TTT|
|P|P|G|I|F|K|S|S|C|Y|I|D|V|R|W|F|
| | | | | | | | | | | | | | |471|
| | | | | | | | | | | | | | |157|
|CCC|TTT|GAT|GTG|CAG|CAC|TGC|AAA|CTG|AAG|TTT|GGG|TCC|TGG|TCT|TAC|
|P|F|D|V|Q|H|C|K|L|K|F|G|S|W|S|Y|
| | | | | | | | | | | | | | |519|
| | | | | | | | | | | | | | |173|
|GGA|GGC|TGG|TCC|TTG|GAT|CTG|CAG|ATG|CAG|GAG|GCA|GAT|ATC|AGT|GGC|
|G|G|W|S|L|D|L|Q|M|Q|E|A|D|I|S|G|
| | | | | | | | | | | | | | |567|
| | | | | | | | | | | | | | |189|
|TAT|ATC|CCC|AAT|GGA|GAA|TGG|GAC|CTA|GTG|GGA|ATC|CCC|GGC|AAG|AGG|
|Y|I|P|N|G|E|W|D|L|V|G|I|P|G|K|R|
| | | | | | | | | | | | | | |615|
| | | | | | | | | | | | | | |205|
|AGT|GAA|AGG|TTC|TAT|GAG|TGC|TGC|AAA|GAG|CCC|TAC|CCC|GAT|GTC|ACC|
|S|E|R|F|Y|E|C|C|K|E|P|Y|P|D|V|T|
| | | | | | | | | | | | | | |663|
| | | | | | | | | | | | | | |221|
|TTC|ACA|GTG|ACC|ATG|CGC|CGC|AGG|ACA|CTC|TAC|TAT|GGC|CTC|AAC|CTG|
|F|T|V|T|M|R|R|R|T|L|Y|Y|G|L|N|L|
| | | | | | | | | | | | | | |711|
| | | | | | | | | | | | | | |237|
|CTG|ATC|CCC|TGT|GTG|CTC|ATC|TCC|GCC|CTG|GCC|CTG|CTG|GTG|TTC|CTG|
|L|I|P|C|V|L|I|S|A|L|A|L|L|V|F|L|
| | | | | | | | | | | | | | |759|
| | | | | | | | | | | | | | |253|
|CTT|CCT|GCA|GAT|TCC|GGG|GAG|AAG|ATT|TCC|CTG|GGG|ATA|ACA|GTC|TTA|
|L|P|A|D|S|G|E|K|I|S|L|G|I|T|V|L|
| | | | | | | | | | | | | | |807|
| | | | | | | | | | | | | | |269|

```
                                                                                              855
                      274                                                                     285
CTC TCT CTT ACC TTC ATG CTG CTC GTG GCT GAG ATC ATG CCC GCA
 L   S   L   T   F   M   L   L   V   A   E   I   M   P   A 903
                                                                                              301
ACA TCC GAT TCG GTA CCA TTG ATA GCC CAG TAC TTC GCC AGC ACC ATG
 T   S   D   S   V   P   L   I   A   Q   Y   F   A   S   T   M 951
                                                                                              317
ATC ATC GTG GGC CTC TCG GTG GTG GTG ATC GTG CTG CAG TAC
 I   I   V   G   L   S   V   V   V   I   V   L   Q   Y 999
                                                                                              333
CAC CAC GAC CCC GAC GGC AAG ATG CCC AAG TGG ACC AGA GTC
 H   H   D   P   D   G   K   M   P   K   W   T   R   V 1047
                                                                                              349
ATC CTT CTG AAC TGG TGC GCG TGG TTC CTG CGA ATG AAG AGG CCC GGG
 I   L   L   N   W   C   A   W   F   L   R   M   K   R   P   G 1095
                                                                                              350
GAG GAC AAG GTG CGC CCG GCC TGC CAG CAC AAG CAG CGG CGC TGC AGC
 E   D   K   V   R   P   A   C   Q   H   K   Q   R   R   C   S 1143
                                                                                              366
CTG GCC AGT GTG GAG ATG AGC GCC GTG GCG CCG CCG CCC GCC AGC AAC
 L   A   S   V   E   M   S   A   V   A   P   P   P   A   S   N
```

```
GGG AAC CTG CTG TAC ATC GGC TTC CGC GGC CTG GAC GGC GTG CAC TGT    1191
 G   N   L   L   Y   I   G   F   R   G   L   D   G   V   H   C     382

GTC CCG ACC CCC GAC TCT GGG GTA GTG TGT GGC CGC ATG GCC TGC TCC    1239
 V   P   T   P   D   S   G   V   V   C   G   R   M   A   C   S     398

CCC ACG CAC GAT GAG CAC CTC CTG GGG CAA CCC CCC GAG GGG AAC        1287
 P   T   H   D   E   H   L   L   G   Q   P   P   E   G            414

GAC CAC TTG GCC AAG ATC CTG GAG GAG GTC TAC ATT GCC AAC            1335
 D   H   L   A   K   I   L   E   E   V   Y   I   A   N            430

CGC TTC CGC TGC CAG GAC GAA AGC GAG GCG GTC TGC AGC GAG TGG AAG    1383
 R   F   R   C   Q   D   E   S   E   A   V   C   S   E   W   K     446

TTC GCC GAC TGT GTG GAC CGC CTG TGC CTC ATG GCC TTC TCG GTC        1431
 F   A   D   C   V   D   R   L   C   L   M   A   F   S   V         462

TTC ACC ATC ATC TGC ACC ATC CTG ATG TCG GCT CCC AAC TTC            1479
 F   T   I   I   C   T   I   L   M   S   A   P   N   F            478

GTG GAG GCC GTG TCC AAA GAC TTT GCG TAACCACGCCTGGTTCTGTACATGTGG
 V   E   A   V   S   K   D   F   A

AAAACTCACAGATGGGCAAGCGCTTTGGCTTGGCGGAGATTCGGGCCGGAA
```

FIG. 2D

VARIANT HUMAN α7 ACETYLCHOLINE RECEPTOR SUBUNIT, AND METHODS OF PRODUCTION AND USES THEREOF

TECHNICAL FIELD

The invention relates generally to receptor proteins and to DNA and RNA molecules encoding therefor. In particular, the invention relates to a variant human α7 subunit in which there is a substitution of the valine-274 position of the wild-type human α7 subunit. The invention also relates to DNA and RNA molecules that encode the variant human α7 subunit, as well as to methods of using the variant subunit to identify compounds that interact with it.

BACKGROUND OF THE INVENTION

This background considers the variant α7 subunit as it relates to the nicotinic acetylcholine receptor (nAChR). The nAChR is comprised of transmembrane polypeptide subunits that form a cation-selective ion channel gated by acetylcholine (ACh) and other ligands. The hydrophobic transmembrane 2 ("TM-2") region from each subunit is believed to form the wall of the ion channel.

Two of the more prominent nAChRs in brain are those containing α4 subunits and those containing α7 subunits (Sargent (1993) Annu. Rev. Neurosci. 16:403–443; Court et al. (1995) Alzheimer Disease and Associated Disorders 9:6–14). Mutations of the α4 and α7 subunits may underlie some diseases of the nervous system. For example, mutations of the α4 subunit have been associated with some forms of epilepsy (Beck et al. (1994) Neurobiol. Disease 1:95–99; Steinlein et al. (1995) Nature Genetics 11:201–203). Additionally, α7-containing nAChR may be involved in sensory processing related to schizophrenia (Freedman et al. (1995) Biol. Psych. 38:22–33; Rollins et al. (1995) Schizophr. Res. 15:183; Stevens et al. (1995) Psychopharmacol. 119:163–170), cytoprotection (Donnelly-Roberts et al. (1996) Brain Res. 719:36–44; Akaike et al. (1994) Brain Res. 644:181–187; Martin et al. (1994) Drug Dev. Res. 31:135–141; Quik et al. (1994) Brain Res. 655:161–167), and neurite growth and innervation (Chan et al. (1993) Neurosci. 56:441–451; Pugh et al. (1994) J. Neurosci. 14:889–896; Freeman (1977) Nature 269:218–222; Broide et al. (1995) Neurosci. 67:83–94).

A splice variant involving the TM-2 region of the α7 subunit has been detected in bovine chromaffin cells (García-Guzmán et al. (1995) Eur. J. Neurosci. 7:647–655), and a naturally-occurring mutation of a protein homologous to the α7 subunit found in *Caenorhabditis elegans*, leads to neurodegeneration (Treinin et al. (1995) Neuron 14:871–877). The latter is a single amino acid mutation in the TM-2 region similar to the chick α7 valine-251 to threonine ("c-α7V251T") mutation, one of several mutations artificially introduced into the chick α7 subunit to facilitate the study of α7 nAChR structure and subunit function (Bertrand et al. (1995) Sem. Neurosci. 7:75–90).

Compared to the chick α7 wild-type ("c-α7WT") nAChR, c-α7V251T (also referred to as α7-4) retained high calcium permeability but desensitized slowly, and was 180-fold more sensitive to ACh. In addition, the c-α7V251T nAChR responded to dihydro-β-erythroidine ("DHβE"), normally an nAChR antagonist at α7 and other wild-type nAChR, as if it were an agonist (Galzi et al. (1992) Nature 359:500–505; Bertrand et al. (1993) Proc. Natl. Acad. Sci. USA 90:6971–6975). These studies have led to a model delineating the structure of the pore-lining TM-2 region, and the hypothesis that specific mutations within the TM-2 region can generate ligand-gated ion channels that conduct current in the receptor-desensitized state in addition to the normal receptor-activated state (Bertrand et al. (1995), supra; Bertrand et al. (1992) Proc. Natl. Acad. Sci. USA 89:1261–1265; Galzi et al. (1995) Neuropharmacol. 34:563–582).

Although the chick α7 nAChR is pharmacologically similar to the mammalian α7 nAChR, there are significant differences. For example, 1,1-dimethyl-4-phenylpiperazinium ("DMPP") is a very weak partial agonist in the chick α7 nAChR, but is a highly efficacious agonist at the human α7 nAChR (Peng et al. (1994) Mol. Pharmacol. 45:546–554). Despite these differences, it would be expected that amino acid changes in the human α7 nAChR that are analogous to those in the chick α7 nAChR, particularly in critical TM-2 amino acids, would result in similar pharmacological and electrophysiological changes.

SUMMARY OF THE INVENTION

The present invention relates to a variant human α7 subunit in which valine-274 has been changed in analogy with the corresponding chick receptor variant. This variant is analogous to the chick α7V251T variant with regard to the relative position of the amino acid substitution in the TM-2 region. However, the variant human α7 subunit exhibits unexpectedly different pharmacological and electrophysiological characteristics.

The α7 subunit combines with itself and may combine with other subunits to create various nicotinic acetylcholine receptors. The possibility of combination with yet other proteins, which may or may not be identified as components of other classes of receptor, is not necessarily excluded.

Accordingly, in one embodiment, a DNA molecule or fragments thereof is provided, wherein the DNA molecule encodes a variant human α7 subunit in which the valine-274 has been replaced.

In another embodiment, a recombinant vector comprising such a DNA molecule, or fragments thereof, is provided.

In another embodiment, the subject invention is directed to a variant human α7 subunit in which the valine-274 has been replaced.

In still other embodiments, the invention is directed to messenger RNA encoded by the DNA, recombinant host cells transformed or transfected with vectors comprising the DNA or fragments thereof and methods of producing recombinant polypeptides for the treatment of neurodegenerative processes, enzymatic function, affective disorders and immunofunction, using such cells.

In another embodiment, compounds such as antagonists are provided, as well as antisense polynucleotides, which are useful in treating conditions such as neurodegenerative processes, enzymatic function, affective disorders and immunofunction. Methods of treating individuals using these compounds and antisense polynucleotides also are provided.

In yet another embodiment, methods and reagents are provided for detecting the α7 variant.

In yet another embodiment, the invention is directed to a method of expressing the human α7 subunit variant in a cell to produce the resultant α7 variant.

In a further embodiment, the invention is directed to a method of identifying compounds that modulate the subunit or receptors containing the subunit and to a method of identifying cytoprotective or other therapeutic compounds using such cells.

These and other embodiments of the present invention will readily occur to those of ordinary skill in the art in view of the disclosure herein.

BRIEF DESCRIPTION OF THE FIGURES

FIGS. 1(A–C) depicts the strategy for generating the human α7V274T AChR variant DNA using polymerase chain reaction.

FIGS. 2A–2D show the nucleotide sequence (SEQ ID NO: 1) of the human α7 cDNA containing the V274T mutation. The threonine mutation is shown in bold and the restriction sites EcoRV and Kpn1 are shown underlined. Also shown is the deduced amino acid sequence (SEQ ID NO: 2) of the human α7V274T subunit variant derived from the cDNA. The V274T alteration is underlined.

DETAILED DESCRIPTION OF THE INVENTION

Figure 3A:
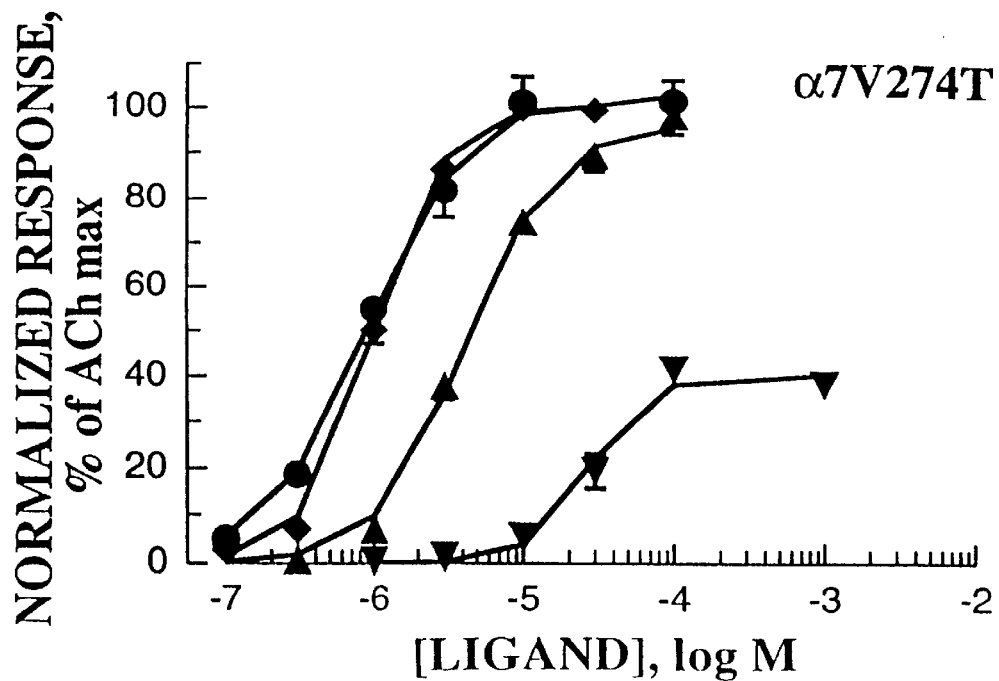
FIG. 3 graphically compares the concentration-response relationships for ACh (diamonds), (−)-nicotine (circles), GTS-21 (triangles pointing up) and ABT-089 (triangles pointing down) using human α7V274T nAChR (solid symbols) and human α7 wild-type nAChR (open symbols) expressed in Xenopus oocytes.

The practice of the present invention will employ, unless otherwise indicated, conventional techniques of molecular biology, microbiology, recombinant DNA technology, electrophysiology, and pharmacology, that are within the skill of the art. Such techniques are explained fully in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); Perbal, B., *A Practical Guide to Molecular Cloning* (1984); the series, *Methods In Enzymology* (S. Colowick and N. Kaplan eds., Academic Press, Inc.); *Transcription and Translation* (Hames et al. eds. 1984); *Gene Transfer Vectors For Mammalian Cells* (J. H. Miller et al. eds. (1987) Cold Spring Harbor Laboratory, Cold Spring Harbor, N.Y.); Scopes, *Protein Purification: Principles and Practice* (2nd ed., Springer-Verlag); and PCR: *A Practical Approach* (McPherson et al. eds. (1991) IRL Press).

All patents, patent applications and publications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "an amplification primer" includes two or more such primers, reference to "a receptor subunit" includes more than one such subunit, and the like.

A. Definitions

In describing the present invention, the following terms will be employed, and are intended to be defined as indicated below.

The term "AChR" intends a receptor for the neurotransmitter acetylcholine ("ACh"). AChRs are broadly subclassified as nicotinic or muscarinic. These types differ in their pharmacology, structures, and signal transduction mechanisms.

The term "nAChR" intends a nicotinic acetylcholine receptor. Although nAChRs of various subunit structures are best known in muscle cells, neurons, and chromaffin cells, they are not necessarily excluded from other cells types (e.g., glial cells, mast cells, blood cells, fibroblasts, etc.).

The term "nAChR subunit" intends a proteinaceous molecule which can combine with other such molecules in the formation of a nAChR. For example, the muscle nAChR is believed to be a pentamer comprised of four types of transmembrane subunit: two α1 subunits, one β1 subunit, one δ subunit and one γ or ε subunit depending upon the nAChR form. Neuronal nAChR analogously are also thought to be pentameric and comprised of related but different subunits. At present, eight neuronal α subunits (α2–α9) and three neuronal β subunits (β2–β4) have been isolated. Some neuronal nAChRs appear to require at least one α subunit and at least one β subunit for a functional complex (i.e., ion channel response to ACh or other agonists). Some subunits, however, may self-assemble to form "homooligomeric" nAChR, as in the case of α7 nAChR in Xenopus oocytes and in transfected mammalian cells. Although the combination of nAChR subunits with subunits related to other types of receptor (e.g., other classes of ligand-gated ion channel) has not been demonstrated, it is within the scope of the present invention that such combinations are possible.

The term "wild-type" (abbreviated "WT") intends the typical, usual or most common form as it occurs in nature. The human wild-type α7 nAChR as used herein was described in Doucette-Stamm et al. (1993) *Drug Dev. Res.* 30: 252–256. An abbreviation of the form "α7XnnnO" intends an α7 subunit in which the amino acid X, located at position nnn relative to the wild type sequence, has been replaced by amino acid 0. Thus, for example, the chick α7V251T subunit indicates the chick α7 subunit in which the valine located at position 251 in the wild type receptor has been replaced by a threonine.

A "nicotinic cholinergic agonist" is a compound that binds to and activates a nicotinic acetylcholine receptor. By "activates" is intended the elicitation of one or more pharmacological, physiological, or electrophysiological responses. Such a response includes, but is not limited to, cell membrane depolarization and increased permeability to Ca$^{2+}$ and other cations.

A "nicotinic cholinergic antagonist" is a substance that binds to a nicotinic acetylcholine receptor and prevents agonists from activating the receptor. Pure antagonists do not activate the receptor, but some substances may have mixed agonist and antagonist properties. Nicotinic cholinergic channel blockers block the ability of agonists to elicit current flow through the nicotinic acetylcholine receptor channel, but do so by blocking the channel rather than by preventing agonists from binding to and activating the receptor.

A "nicotinic cholinergic modulator" intends a substance that influences the activity of the nicotinic acetylcholine receptor through interaction at one or more sites other than the classic agonist binding site. The modulator may itself increase or decrease receptor activity, or may influence agonist activity (for example, potentiating responses) without itself eliciting an overt change in channel current. A single substance can have different properties at different nicotinic acetylcholine receptor subtypes, for example, being an agonist at one receptor and antagonist at another, or an antagonist at one and a channel blocker at another.

By "nAChR regulator" is intended a substance that may act as an agonist, antagonist, channel blocker or modulator.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, such as by methylation and/or by capping, and unmodified forms of the polynucleotide. The term "variant" is used to refer to an oligonucleotide sequence which differs from the related wild-type sequence in one or more nucleotides. Such a variant oligonucleotide is expressed as a protein variant which, as used herein, indicates a polypeptide sequence that differs from the wild-type polypeptide in the substitution, insertion or deletion of one or more amino acids. The variant polypeptide differs in primary structure (amino acid sequence), but may or may not differ significantly in secondary or tertiary structure or in function relative to the wild-type.

The term "mutant" generally refers to an organism or a cell displaying a new genetic character or phenotype as the result of change in its gene or chromosome. In some instances, however, "mutant" may be used in reference to a variant protein or oligonucleotide and "mutation" may refer to the change underlying the variant.

"Polypeptide" and "protein" are used interchangeably herein and indicate a molecular chain of amino acids linked through peptide bonds. The terms do not refer to a specific length of the product. Thus, peptides, oligopeptides, and proteins are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide.

A "functionally conservative mutation" as used herein intends a change in a polynucleotide encoding a derivative polypeptide in which the activity is not substantially altered compared to that of the polypeptide from which the derivative is made. Such derivatives may have, for example, amino acid insertions, deletions, or substitutions in the relevant molecule that do not substantially affect its properties. For example, the derivative can include conservative amino acid substitutions, such as substitutions which preserve the general charge, hydrophobicity/hydrophilicity, side chain moiety, and/or stearic bulk of the amino acid substituted, for example, Gly/Ala, Val/Ile/Leu, Asp/Glu, Lys/Arg, Asn/Gln, Thr/Ser, and Phe/Trp/Tyr.

By the term "structurally conservative mutant" is intended a polynucleotide containing changes in the nucleic acid sequence but encoding a polypeptide having the same amino acid sequence as the polypeptide encoded by the polynucleotide from which the degenerate variant is derived. This can occur because a specific amino acid may be encoded by more than one "codon," or sequence of three nucleotides.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vectors or other transfer DNA, immaterial of the method by which the DNA is introduced into the cell or the subsequent disposition of the cell. The terms include the progeny of the original cell which has been transfected. Cells in primary culture as well as cells such as oocytes also can be used as recipients.

A "vector" is a replicon in which another polynucleotide segment is attached, such as to bring about the replication and/or expression of the attached segment. The term includes expression vectors, cloning vectors, and the like.

A "coding sequence" is a polynucleotide sequence that is transcribed into mRNA and/or translated into a polypeptide. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences. Variants or analogs may be prepared by the deletion of a portion of the coding sequence, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences. A coding sequence may be operably linked to control sequences that direct the transcription of the polynucleotide whereby said polynucleotide is expressed in a host cell.

The term "transfection" refers to the insertion of an exogenous polynucleotide into a host cell, irrespective of the method used for the insertion, or the molecular form of the polynucleotide that is inserted. The insertion of a polynucleotide per se and the insertion of a plasmid or vector comprised of the exogenous polynucleotide are included. The exogenous polynucleotide may be directly transcribed and translated by the cell, maintained as a nonintegrated vector, for example, a plasmid, or alternatively, may be stably integrated into the host genome. "Transfection" generally is used in reference to a eukaryotic cell while the term "transformation" is used to refer to the insertion of a polynucleotide into a prokaryotic cell. "Transformation" of a eukaryotic cell also may refer to the formation of a cancerous or tumorigenic state.

The term "isolated," when referring to a polynucleotide or a polypeptide, intends that the indicated molecule is present in the substantial absence of other similar biological macromolecules. The term "isolated" as used herein means that at least 75 wt. %, more preferably at least 85 wt. %, more preferably still at least 95 wt. %, and most preferably at least 98 wt. % of a composition is the isolated polynucleotide or polypeptide. An "isolated polynucleotide" that encodes a particular polypeptide refers to a polynucleotide that is substantially free of other nucleic acid molecules that do not encode the subject polypeptide; however, the molecule may include functionally and/or structurally conservative mutations as defined herein.

A "test sample" as used herein intends a component of an individual's body which is a source of the α7 subunit. These test samples include biological samples which can be evaluated by the methods of the present invention described herein and include body fluids such as whole blood, tissues and cell preparations.

The following single-letter amino acid abbreviations are used throughout the text:

| Alanine | A | Arginine | R |
| Asparagine | N | Aspartic acid | D |
| Cysteine | C | Glutamine | Q |
| Glutamic acid | E | Glycine | G |
| Histidine | H | Isoleucine | I |
| Leucine | L | Lysine | K |
| Methionine | M | Phenylalanine | F |
| Proline | P | Serine | S |
| Threonine | T | Tryptophan | W |
| Tyrosine | Y | Valine | V |

B. General Methods

A variant human α7 subunit, a polynucleotide encoding the variant subunit, and methods of making the variant subunit are provided herein. The invention includes not only the variant subunit but also methods for screening compounds using the variant subunit and cells expressing the variant subunit. Further, polynucleotides and antibodies which can be used in methods for detection of the variant subunit, as well as the reagents useful in these methods, are provided. Compounds and polynucleotides useful in regulating the variant and its expression also are provided as disclosed hereinbelow.

In one preferred embodiment, the polynucleotide encodes a human α7 subunit variant in which the valine-274 of the wild-type α7 subunit has been replaced. Preferably, the polynucleotide encodes a human α7 subunit in which the valine-274 has been replaced by a threonine, or a conservative substitution for the threonine, e.g., serine.

The human α7 variant nAChR exhibits both similar and unexpectedly different properties relative to other structurally related nAChRs. For example, as with the chick α7V251T variant, the human α7V274T variant's responses to cholinergic agonists decay slowly compared to the human wild-type α7 nAChR responses. In addition, human α7V274T is about two orders of magnitude more sensitive to cholinergic receptor agonists such as nicotine and ACh compared to the wild-type.

Figure 5:
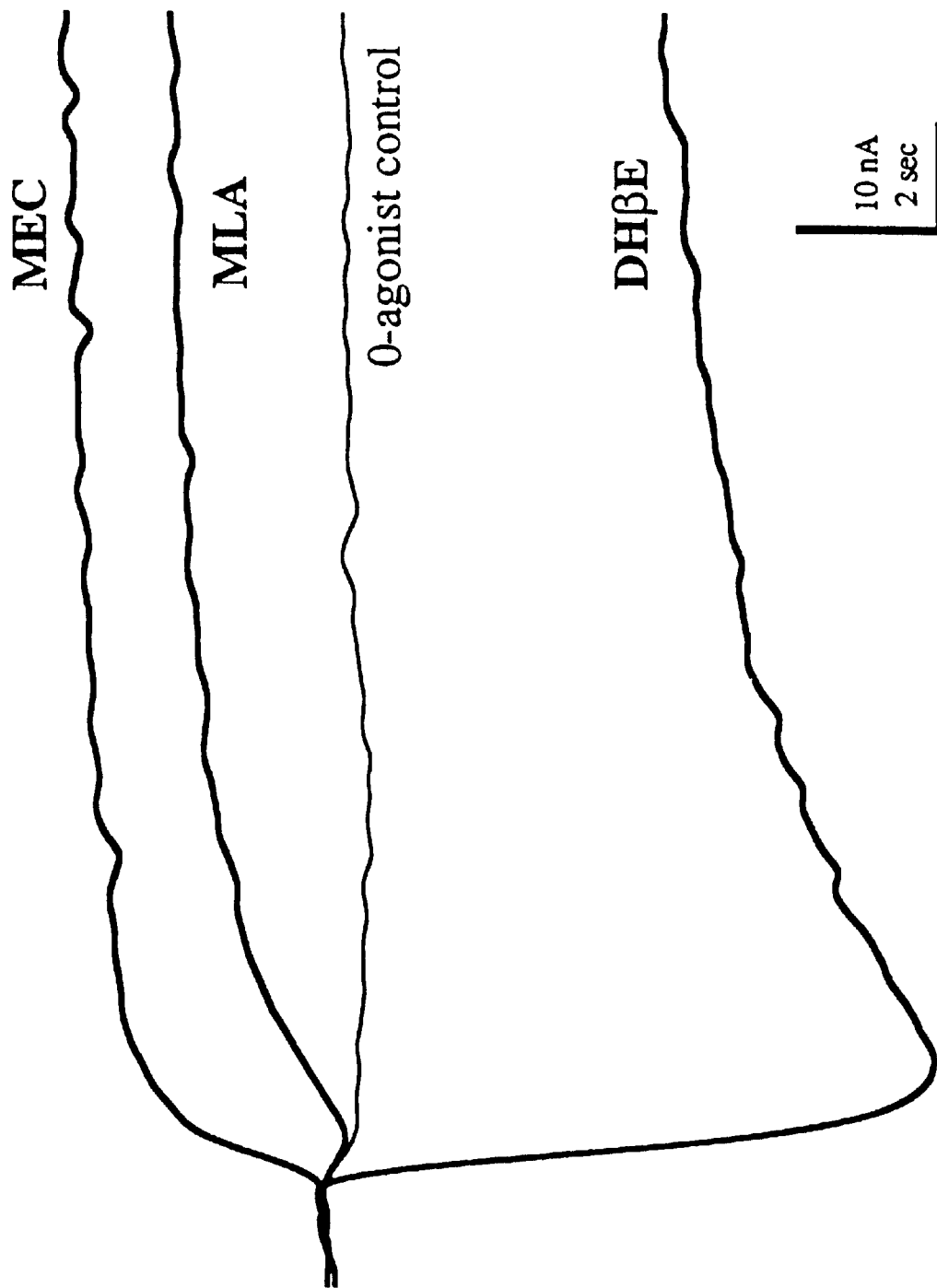
FIG. 5 graphically depicts the responses of human α7V274T to nAChR antagonists wherein MEC is mecamylamine (10 μM), MLA is methyllycaconitine (10 nM), and DHβE is dihydro-β-erythroidine (10 μM). The 0-agonist control was bathing solution without drug and was applied for 20 seconds. The small 0-agonist control responses were measured in each human α7V274T oocyte and subtracted from agonist responses when data were tabulated.
Figure 6:
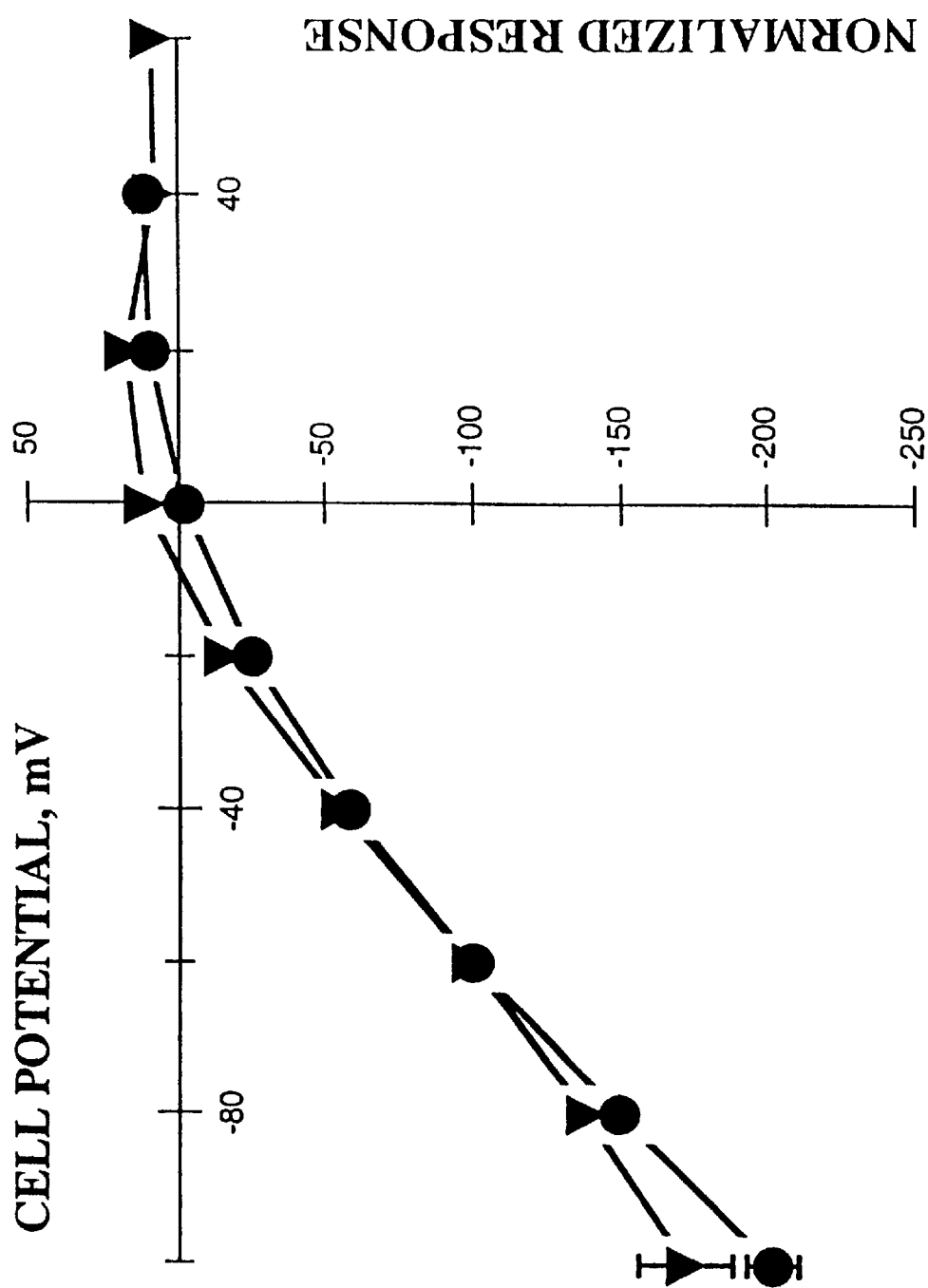
FIG. 6 graphically depicts the current versus voltage relationship of responses to 10 μM ACh of the human α7V274T expressed in *Xenopus laevis* oocytes, wherein the circles represent responses measured in modified Barth's solution containing 10 mM Ba$^{2+}$ (90 mM NaCl, 1 mM KCl, 0.66 mM NaNO$_3$, 10 mM BaCl$_2$, 2.4 mM NaHCO$_3$, 2.5 mM sodium pyruvate, and 10 mM Na-HEPES buffer, final pH 7.55) to prevent activation of Ca$^{2+}$-dependent secondary responses (see Briggs et al. (1995) *Neuropharmacol.* 34:583–590) and the triangles represent responses measured in "OR2" solution with atropine (82.5 mM NaCl, 2.5 mM KCl, 2.5 mM CaCl$_2$, 1 mM MgCl$_2$, 0.5 μM atropine, and 5 mM Na-HEPES buffer, final pH 7.4) to replicate the conditions of Galzi et al. (1992) *Nature* 359:500–505.

The human and chick receptor variants differ pharmacologically, for example, in that human α7V274T is weakly activated by dihydro-β-erythroidene (DHβE) while chick α7V251T is strongly activated (66%; FIG. 5 and Galzi et al. (1992), supra). In addition, d-tubocurarine is a potent antagonist of human α7V274T compared to an activator of the related chick α7L247T mutant (Bertrand et al. (1992), supra). The human and chick α7 receptor variants are electrophysiologically different as well. For example, the chick α7V251T nAChR does not exhibit inward current rectification (Galzi et al. (1992), supra), unlike both chick and human α7 wild-type nAChR which exhibit strong inward rectification (Galzi et al. (1992), supra, and Briggs et al. (1995) Neuropharmacol. 34: 583–590). The human α7V274T nAChR, in contrast to the chick α7V251T nAChR, rectifies above 0 mV similarly to the wild-type receptor (FIG. 6).

DNA encoding the variant human α7 subunit can be derived from genomic or cDNA, prepared by synthesis, or by a combination of techniques. The DNA can then be used to express the variant human α7 subunit or as a template for the preparation of RNA using methods well known in the art (see, Sambrook et al., supra)

One method for obtaining the desired DNA involves isolating cDNA encoding the wild-type human α7 nAChR subunit as described by Doucette-Stamm et al. (1993), supra. The wild-type cDNA thus obtained is then modified and amplified using the polymerase chain reaction ("PCR") and mutated primer sequences to obtain the DNA encoding the human α7 variant nAChR subunit. More particularly, PCR employs short oligonucleotide primers (generally 10–20 nucleotides in length) that match opposite ends of a desired sequence within the wild-type DNA molecule. The sequence between the primers need not be known. The initial template can be either RNA or DNA. If RNA is used, it is first reverse transcribed to cDNA. The cDNA is then denatured, using well known techniques such as heat, and appropriate oligonucleotide primers are added in molar excess.

Primers bearing the mutation will hybridize to the wild-type polynucleotide at a temperature slightly below that of the wild-type primer-polynucleotide duplex. The primer can be made specific by keeping primer length and base composition within relatively narrow limits, and by keeping the mutant base or bases centrally located (Zoler et al. (1983) Meth. Enzymol. 100:468). Primer extension is effected using DNA polymerase in the presence of deoxynucleotide triphosphates or nucleotide analogs. The resulting product includes the respective primers at their 5'-termini, covalently linked to the newly synthesized complements of the original strands. The replicated molecule is again denatured, hybridized with primers, and so on, until the product is sufficiently amplified. Such PCR methods are described in e.g., U.S. Pat. Nos. 4,965,188; 4,800,159; 4,683,202; 4,683,195; incorporated herein by reference in their entireties. The product of the PCR is cloned and the clones containing the mutated DNA, derived by segregation of the primer extended strand, selected. Selection can be accomplished using the mutant primer as a hybridization probe.

Alternatively, the wild-type DNA may be obtained from an appropriate DNA library. DNA libraries may be probed using the procedure described by Grunstein et al. (1975) Proc. Natl. Acad. Sci. USA 73:3961.

Alternatively still, the α7 variant could be generated using an RT-PCR (reverse transcriptase—polymerase chain reaction) approach starting with human RNA. For example, single-stranded cDNA is synthesized from human RNA (approx. 1.5 μg) as the template using standard reverse transcriptase procedures. Next, the cDNA is amplified in two segments and the mutation is introduced using PCR and two pairs of primers. For example, the internal primers are designed to carry the codon for threonine (T) or other desired change in place of the wild-type valine (V) at position 274 (see also Example 1 p. 28 and FIG. 1). The products of the two PCR reactions are combined using the 3' and 5' end primers to re-amplify the full length coding sequence of the α7 variant. This is but one example of the generation of α7V274T from a human brain template.

Synthetic oligonucleotides may be prepared using an automated oligonucleotide synthesizer such as that described by Warner (1984) *DNA* 3:401. If desired, the synthetic strands may be labelled with $^{32}$P by treatment with polynucleotide kinase in the presence of $^{32}$P-ATP, using standard conditions for the reaction. DNA sequences, including those isolated from genomic or cDNA libraries, may be modified by known methods which include site-directed mutagenesis as described by Zoller (1982) *Nucleic Acids Res.* 10:6487. Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. Culture of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labelled synthetic probe at temperatures and conditions suitable for hybridization with the correct strand, but not with the unmodified sequence. The sequences which have been identified by hybridization are recovered and cloned. Alternatively, it may be necessary to identify clones by sequence analysis if there is difficulty in distinguishing the variant from wild-type by hybridization. In any case, the DNA would be sequence-confirmed.

Once produced, the DNA may then be incorporated into a cloning vector or an expression vector for replication in a suitable host cell. Vector construction employs methods known in the art. Generally, site-specific DNA cleavage is performed by treating with suitable restriction enzymes under conditions which generally are specified by the manufacturer of these commercially available enzymes. After incubation with the restriction enzyme, protein is removed by extraction and the DNA recovered by precipitation. The cleaved fragments may be separated using, for example, polyacrylamide or agarose gel electrophoresis methods, according to methods known by those of skill in the art.

Sticky end cleavage fragments may be blunt ended using *E. coli* DNA polymerase 1 (Klenow) in the presence of the appropriate deoxynucleotide triphosphates (dNTPs) present in the mixture. Treatment with S1 nuclease also may be used, resulting in the hydrolysis of any single stranded DNA portions.

Ligations are performed using standard buffer and temperature conditions using T4 DNA ligase and ATP. Alternatively, restriction enzyme digestion of unwanted fragments can be used to prevent ligation.

Standard vector constructions generally include specific antibiotic resistance elements. Ligation mixtures are transformed into a suitable host, and successful transformants selected by antibiotic resistance or other markers. Plasmids from the transformants can then be prepared according to methods known to those in the art usually following a chloramphenicol amplification as reported by Clewell et al. (1972) *J. Bacteriol.* 110:667 may be added. The DNA is isolated and analyzed usually by restriction enzyme analysis and/or sequencing. Sequencing may be by the well-known dideoxy method of Sanger et al. (1977) *Proc. Natl. Acad. Sci. USA* 74:5463) as further described by Messing et al. (1981) *Nucleic Acid Res.* 9:309, or by the method reported by Maxam et al. (1980) *Meth. Enzymol.* 65:499. Problems with band compression, which are sometimes observed in GC rich regions, are overcome by use of, for example, T-deazoguanosine or inosine, according to the method reported by Barr et al. (1986) *Biotechniques* 4:428.

Host cells are genetically engineered with the vectors of this invention which may be a cloning vector or an expression vector. The vector may be in the form of a plasmid, a viral particle, a phage, etc. The engineered host cells can be cultured in conventional nutrient media modified as appropriate for activating promoters, selecting transformants/transfectants or amplifying the subunit-encoding polynucleotide. The culture conditions, such as temperature, pH and the like, generally are similar to those previously used with the host cell selected for expression, and will be apparent to those of skill in the art.

Both prokaryotic and eukaryotic host cells may be used for expression of desired coding sequences when appropriate control sequences that are compatible with the designated host are used. For example, among prokaryotic hosts, *Escherichia coli* is frequently used. Also, for example, expression control sequences for prokaryotes include but are not limited to promoters, optionally containing operator portions, and ribosome binding sites. Transfer vectors compatible with prokaryotic hosts can be derived from, for example, the plasmid pBR322 that contains operons conferring ampicillin and tetracycline resistance, and the various pUC vectors, that also contain sequences conferring antibiotic resistance markers. These markers may be used to obtain successful transformants by selection. Commonly used prokaryotic control sequences include but are not limited to the lactose operon system (Chang et al. (1977) *Nature* 198:1056), the tryptophan operon system (reported by Goeddel et al. (1980) *Nucleic Acid Res.* 8:4057) and the lambda-derived Pl promoter and N gene ribosome binding site (Shimatake et al. (1981) *Nature* 292:128), the hybrid Tac promoter (De Boer et al. (1983) *Proc. Natl. Acad. Sci. USA* 292:128) derived from sequences of the trp and lac UV5 promoters. The foregoing systems are particularly compatible with *E. coli*; however, other prokaryotic hosts such as strains of Bacillus or Pseudomonas may be used if desired.

Eukaryotic hosts include yeast and mammalian cells in culture systems. *Pichia pastoris, Saccharomyces cerevisiae* and *S. carlsbergensis* are commonly used yeast hosts. Yeast-compatible vectors carry markers that permit selection of successful transformants by conferring protrophy to auxotrophic mutants or resistance to heavy metals on wild-type strains. Yeast compatible vectors may employ the 2-$\mu$ origin of replication (Broach et al. (1983) *Meth. Enzymol.* 101:307), the combination of CEN3 and ARS1 or other means for assuring replication, such as sequences that will result in incorporation of an appropriate fragment into the host cell genome. Control sequences for yeast vectors are known in the art and include but are not limited to promoters for the synthesis of glycolytic enzymes, including the promoter for 3-phosphoglycerate kinase. See, for example, Hess et al. (1968) *J. Adv. Enzyme Reg.* 7:149, Holland et al. (1978) *Biochemistry* 17:4900 and Hitzeman (1980) *J. Biol. Chem.* 255:2073. For example, some useful control systems are those that comprise the glyceraldehyde-3-phosphate dehydrogenase (GAPDH) promoter or alcohol dehydrogenase (ADH) regulatable promoter, terminators also derived from GAPDH, and, if secretion is desired, leader sequences from yeast alpha factor. In addition, the transcriptional regulatory region and the transcriptional initiation region which are operably linked may be such that they are not naturally associated in the wild-type organism.

Mammalian cell lines available as hosts for expression are known in the art and are available from depositories such as the American Type Culture Collection. These include but are not limited to HeLa cells, human embryonic kidney (HEK) cells, Chinese hamster ovary (CHO) cells, baby hamster kidney (BHK) cells, and others. Suitable promoters for mammalian cells also are known in the art and include viral promoters such as that from Simian Virus 40 (SV40), Rous sarcoma virus (RSV), adenovirus (ADV), bovine papilloma virus (BPV) and cytomegalovirus (CMV). Mammalian cells also may require terminator sequences and poly A addition sequences; enhancer sequences which increase expression also may be included, and sequences which cause amplification of the gene also may be desirable. These sequences are known in the art. Vectors suitable for replication in mammalian cells may include viral replicons, or sequences which ensure integration of the appropriate sequences encoding the variant α7 nAChR subunit into the host genome. An example of such a mammalian expression system is described in Gopalakrishnan et al. (1995), *Eur. J. Pharmacol.-Mol. Pharmacol.* 290: 237–246.

Other eukaryotic systems are also known, as are methods for introducing polynucleotides into such systems, such as amphibian cells using methods described in Briggs et al. (1995) *Neuropharmacol.* 34:583–590, insect cells using methods described in Summers and Smith, *Texas Agricultural Experiment Station Bulletin No.* 1555 (1987), and the like.

The baculovirus expression system can be used to generate high levels of recombinant proteins in insect host cells. This system allows for high level of protein expression, while post-translationally processing the protein in a manner similar to mammalian cells. These expression systems use viral promoters that are activated following baculovirus infection to drive expression of cloned genes in the insect cells (O'Reilly et al. (1992) Baculovirus Expression Vectors: A Laboratory Manual, IRL/Oxford University Press).

Transfection may be by any known method for introducing polynucleotides into a host cell, including packaging the polynucleotide in a virus and transducing a host cell with the virus, by direct uptake of the polynucleotide by the host cell, and the like, which methods are known to those skilled in the art. The transfection procedures selected depend upon the host to be transfected and are determined by the rountineer.

The expression of the variant receptor subunit may be detected by use of a radioligand selective for the receptor. For example, for the nicotinic cholinergic receptor, such a ligand may be $[^{125}I]$α-bungarotoxin. However, any radioligand binding technique known in the art may be used to detect the receptor subunit (see, e.g., Winzor et al. (1995) *Quantitative Characterization of Ligand Binding*, Wiley-Liss, Inc., N.Y.). Alternatively, expression can be detected by utilizing antibodies or functional measurements which are well known to those skilled in the art.

The variant nAChR polypeptide is recovered and purified from recombinant host cell cultures expressing the same by known methods including ammonium sulfate or ethanol precipitation, acid extraction, anion or cation exchange chromatography, phosphocellulose chromatography, hydrophobic interaction chromatography, hydroxyapatite chromatography or lectin chromatography. Protein refolding steps can be used, as necessary, in completing configuration of the protein. Finally, high performance liquid chromatography (HPLC) can be employed for final purification steps.

The human α7 variant polypeptide, or fragments thereof, of the present invention also may be synthesized by conventional techniques known in the art, for example, by chemical synthesis such as solid phase peptide synthesis. In general, these methods employ either solid or solution phase synthesis methods. See, e.g., J. M. Stewart and J. D. Young, *Solid Phase Peptide Synthesis,* 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology,* supra, Vol. 1, for classical solution synthesis.

In one preferred system, either the DNA or the RNA derived therefrom, both of which encode the desired variant human α7 subunit, may be expressed by direct injection into a cell, such as a *Xenopus laevis* oocyte. Using this method, the functionality of the human α7 subunit variant encoded by the DNA or the mRNA can be evaluated as follows (see Dascal (1987) *CRC Crit. Rev. Biochem.* 22:317–387). A variant-encoding polynucleotide is injected into an oocyte for translation into a functional receptor subunit. The function of the expressed variant human α7 nAChR can be assessed in the oocyte by a variety of electrophysiological techniques including intracellular voltage recording, two-electrode voltage clamp, patch clamp methods, and the like. The cation-conducting channel intrinsic to the nAChR opens in response to ACh or other nicotinic cholinergic agonists, permitting the flow of transmembrane current. This current can be monitored directly by voltage clamp techniques or indirectly by intracellular voltage recording, wherein changes in membrane potential due to the induced current are measured. Alternatives can include measurement of ion flux or fluorescent pribes sensitive to transmembrane potential or changes in ion activity.

Receptors expressed in a recombinant host cell may be used to identify compounds that modulate nAChR activity. In this regard, the specificity of the binding of a compound showing affinity for the receptor is demonstrated by measuring the affinity of the compound for cells expressing the receptor or membranes from these cells. This may be done by measuring specific binding of labeled (e.g., radioactive) compound to the cells, cell membranes or isolated receptor, or by measuring the ability of the compound to displace the specific binding of a standard labeled ligand. Expression of variant receptors and screening for compounds that bind to, or inhibit the binding of labeled ligand to these cells or membranes provides a method for rapid selection of compounds with high affinity for the receptor. These compounds may be agonists, antagonists or modulators of the receptor.

Expressed receptors also may be used to screen for compounds that modulate nicotinic acetylcholine receptor activity. One method for identifying compounds that modulate nAChR activity, comprises providing a cell that expresses a variant human α7 nicotinic acetylcholine receptor (nAChR) polypeptide having an amino acid substitution at position valine-274 of the wild-type human α7 nAChR polypeptide, combining a test compound with the cell and measuring the effect of the test compound on the variant receptor activity. The cell may be a bacterial cell, a mammalian cell, a yeast cell, an amphibian cell or any other cell expressing the receptor. Preferably, the cell is a mammalian cell or an amphibian cell. Thus, for example, a test compound is evaluated for its ability to elicit an appropriate response, e.g., the stimulation of transmembrane current flow, for its ability to inhibit the response to a cholinergic agonist, or for its ability to modulate the response to an agonist or antagonist.

In addition, expressed receptors may be used to screen compounds that exhibit a cytoprotective effect. Abnormal activation of membrane channels is a potential cause of neurodegenerative disease. In this regard, a number of inherited human disorders are accompanied by neuronal degeneration (Adams et al. (1989) *Degenerative Disease of the Nervous System*, in *Principles of Neurology*, McGraw- Hill, N.Y., pp. 921–967). Many model systems have been used to study the causes of these diseases. For example, mutations in proteins that have extensive sequence similarity to proteins that contribute to the amiloride-sensitive sodium ion channel have been associated with vacuolated neurodegeneration in the nematode *C. elegans* (Canessa et al. (1993) *Nature,*361:467–470; Canessa et al. (1994) *Nature,* 367:463–467; Lingueglia et al. (1993) *FEBS Lett.* 318:95–99; and Voilley et al. (1994) *Proc. Natl. Acad. Sci. USA* 91:247–251). A so-called "gain-of-function" mutation in the deg-3 protein of *C. elegans*, causes vacuolated degeneration of a small set of neurons (Treinin et al. (1995), supra). Studies of this mutation suggested to these investigators that mutation in neuronal acetylcholine receptors may lead to death of specific neuronal populations.

Additionally, the α7 variant can be used to screen for compounds useful in treating disorders such as alterations in sensory gating, immunofunction and neuropathic pain, e.g., pain associated with cancerous conditions, post herpatic neuralgia, diabetic neuropathy and osteoarthritis. Further, the α7 variant could be used to treat or to kill cancerous cells.

Accordingly, nicotinic drugs are considered potential therapeutic agents in several neurodegenerative disorders including, without limitation, Alzheimer's disease, Down's syndrome, kuru, Parkinson's disease, multiple system atrophy, neuropathic pain, immune function, schizophrenia and the like. Activation of the wild type α7 nAChR appears to elicit cytoprotective properties (e.g., reduced cell lysis, see Donnelly-Roberts et al. (1996), supra. However, it is not yet finally established whether a full agonist or partial agonist is preferable, nor, if the latter, what type of partial agonist is best (e.g., one that stabilizes the open and desensitized states or one that stabilizes the open and resting states of the receptor). The variant α7 nAChR can be used to evaluate these questions, and to select among ligands for specific types of partial agonists or specific types of antagonists. That is because this variant α7 nAChR conducts current in the desensitized as well as the open states, unlike the wild type receptor that conducts only in the open state (see Bertrand and Changeux (1995), *Sem. Neurosci.* 7: 75–90). Thus, with the variant human nAChR subunit agonist potency is shifted two orders of magnitude to a level consistent with agonist affinity for the desensitized state. Furthermore, ligands that are partial agonists at the wild type α7 nAChR subunit because of their ability to stabilize desensitized as well as open states would be expected to have increased efficacy at the variant nAChR subunit due to its ability to conduct in the desensitized state. Examples of such potency and efficacy shifts are shown for the human α7V274T nAChR in FIG. 3.

Thus, α7 nAChR ligand pharmacology can be defined in novel ways through the use of the human variant nAChR subunit. Substances could be antagonists at the wild type α7 nAChR due to their ability to stabilize the non-conducting desensitized state, or due to other mechanisms such as stabilizing the resting state or blocking the ion channel. Similar mechanisms could contribute to partial agonism at the wild type α7 nAChR. The ability of a ligand to stabilize the desensitized state could be evaluated by comparing the ligand's potency and efficacy at the variant α7 nAChR (e.g., human α7v274T) to its potency and efficacy at the wild-type α7 nAChR. The interaction of compounds with the nAChR can be identified using several methods, including, but not limited to, electrophysiologic measurement of transmembrane current flow or electrical potential, measurement of the fluorescence of potential- or ion-sensitive dyes, or measurement of radioactive ion flux (e.g. $^{22}Na^+$ or $^{86}Rb^+$) and a variety of α7 nAChR expression systems, for example transfected mammalian cells in culture or injected amphibian cells. This novel definition of α7 nAChR pharmacology coupled with measures of α7 ligand effect on cell or animal functioning could be critical to the development of novel therapeutics. For example, it could be determined whether a ligand that stabilizes the desensitized state of the α7 nAChR subunit (partial agonist or antagonist) is preferable for cytoprotection. Likewise, the type of ligand more or less useful in other nicotinic applications, such as cognition, memory, anxiety, attention, sensory gating (psychoses and schizophrenia), etc. could be evaluated using variant α7 nAChR subunits alone or in combination with other receptor subunits.

In addition to screening test compounds, the expressed variant α7 subunit may be used to investigate mechanisms of cytotoxicity and cytoprotection. The evidence that activation of α7 nAChR is cytoprotective comes from the finding that nAChR agonists elicit cytoprotection in cells expressing the wild-type α7 nAChR subunit and that this cytoprotection is inhibited by selective α7 antagonists (for example see Donnelly-Roberts et al., supra). The mechanism is unknown but may involve the stimulation of $Ca^{2+}$ influx. If so, then the increased $Ca^{2+}$ influx mediated by the variant α7 nAChR, due to maintained $Ca^{2+}$ permeability with prolonged current activation, may augment the cytoprotection. On the other hand, as excessive intracellular $Ca^{2+}$ is known to be cytotoxic, excessive expression or stimulation of the variant α7 nAChR could cause cell death, perhaps as observed in *C. elegans* carrying the endogenous mutation in deg3 analogous to the α7 variant. Alternatively still, the α7 nAChR subunit may also function through mechanisms dependent upon a change in receptor state (e.g., from resting to desensitized conformation), which may influence its interaction with other proteins, but not necessarily dependent upon a change in ion flux or electrical potential. The variant α7 nAChR subunit would be critical in determining such mechanisms as it would allow one to identify ligands that favor different receptor states, and as it provides a tool for manipulating nAChR channel current independently from nAChR conformation and ligand binding.

Cytoprotective or cytotoxic compounds that interact with the variant nAChR may be identified using several methods. One such method comprises providing a cell that expresses a variant human α7 subunit having an amino acid substitution at position valine-274 of the wild-type human α7 nAChR polypeptide, combining a test compound with the cell, and monitoring the cell for an indicator of cytotoxicity. If it is necessary to control spontaneous action of the variant nAChR subunit, it may be stably expressed in a recombinant mammalian cell line under the control of an inducible promoter, e.g., the LacSwitch system which is inducible by isopropylthiogalactoside ("IPTG"). Expression of the variant α7 subunit would be maintained at a low level until induction by the addition of IPTG. Alternatively, with or without an inducible promoter, the transfected cells could be cultured in the presence of an α7 blocker, such as methyllycaconitine ("MLA") or mecamylamine, that would prevent or reduce cytotoxic action. Both blockers are reversible, permitting one to measure the effect of test compound on α7 nAChR function after the blocker is washed out.

Cytoprotective compounds can be identified by their ability to reduce cell death while cytotoxic compounds can be identified by their ability to promote cell death. That these effects are mediated by the α7 subunit, variant or wild type, can be identified by the ability of an α7 blocker to prevent the effect. Cell death, or cytotoxicity, can be monitored by a variety of techniques including but not limited to measurement of cell number or density in the culture, of cell growth rate (e.g. incorporation of labeled nucleotide or amino acid), or of cell integrity for example by uptake of a dye (e.g. trypan blue is excluded by healthy cells, or by inclusion of MTT by healthy cells), or by the release of a cytoplasmic constituent such as lactate dehydrogenase (LDH). Cytoprotective agents may also be screened for their ability to antagonize a variant nAChR to a greater extent than a wild-type nAChR, or for their ability to augment the decay rate of variant nAChR compared to the wild-type nAChR, using methods described in the examples provided below.

In addition, the DNA, or RNA derived therefrom, can be used to design oligonucleotide probes for DNAs that express variant subunits. As used herein, the term "probe" refers to a structure comprised of a polynucleotide, as defined above, which contains a nucleic acid sequence complementary to a nucleic acid sequence present in a target polynucleotide. The polynucleotide regions of probes may be composed of DNA, and/or RNA, and/or synthetic nucleotide analogs. Such probes could be useful in in vitro hybridization assays to distinguish α7 variant from wild-type message, with the proviso that it may be difficult to design a method capable of making such a distinction given the small difference in coding between variant and wild-type. Alternatively, a PCR-based assay could be used to amplify the sample RNA or DNA for sequence analysis.

Furthermore, the α7 subunit or fragment(s) therof can be used to prepare monoclonal antibodies using techniques that are well known in the art. The variant α7 subunit or relevant fragments can be obtained using the recombinant technology outlined below, i.e., a recombinant cell that expresses the subunit or fragments can be cultured to produce quantities of the subunit or fragment that can be recovered and isolated. Alternatively, the variant α7 subunit or fragment(s) thereof can be synthesized using conventional polypeptide synthetic techniques as known in the art. Monoclonal antibodies that display specificity and selectivity for the variant α7 subunit can be labeled with a measurable and detectable moiety, e.g., a fluorescent moiety, radiolabels, enzymes, chemiluminescent labels and the like, and used in in vitro assays. It is theorized that such antibodies could be used to identify variant α7 subunits for immunodiagnostic purposes. For example, antibodies have been generated to detect amyloid β1-40 v. 1-42 in brain tissue, (T. Wisniewski et al. (1996) *Biochem J.* 313:575–580; also see, N. Suzuki et al. (1994) *Science* 264:1336–1340; S. A. Gravina et al. (1995) *J. Biolog. Chem.* 270:7013–7016; and R. S. Turnet et al. (1996) *J. Biolog. Chem.* 271:8966–8970).

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXPERIMENTAL

Materials

Acetylcholine chloride ("ACh"), collagenase Type 1A, d-tubocurarine chloride ("dTC"), gentamicin and mecamylamine hydrochloride ("MEC"), were obtained from Sigma Chemical Company (St. Louis, Mo., U.S.A.). Dihydro-β-erythroidine hydrobromide ("DHBE"), and methyllycaconitine citrate ("MLA") were obtained from Research Biochemicals International (Natick, Mass., U.S.A.). Tricaine (3-aminobenzoic acid ethyl ester methanesulfonate; Finquel) was obtained from Argent Chemical Laboratories (Fisheries Chemical Division, Redmond, Wash., U.S.A.).

Preparation of the Human α7 Wild-Type cDNA

The human α7 subunit cDNA reported by Doucette-Stamm et al. (1993), supra, was modified to include the complete human signal peptide MRCSPGGVWLA-LAASLLHVSLQGEF position 1-25 of (SEQ ID NO: 1)) reported by Elliott et al. (1993) *Soc. Neurosci. Abstr.* 19:69. This oligonucleotide contains an Xho I restriction site (italics) and an ATG initiation codon (bold) followed by the next 28 codons of the human α7 subunit cDNA sequence. It encodes the complete signal peptide and extends to the Hind III site (underlined) present in the α7 subunit cDNA. The Xho I and Hind III sites were flanked with additional nucleotides to make them internal within the molecule. Additionally, the reverse complement of this oligonucleotide was synthesized. The oligonucleotides were annealed together, digested with Xho I and Hind III, and then ligated into a pBluescript® vector containing the human α7 subunit cDNA previously digested with Xho I and Hind III. This created a new cDNA encoding a full length human α7 subunit. The sequence of the new cDNA was confirmed by dideoxy sequencing. The cDNA was excised from pBluescript® with Xho I and Not I, the 5' overhangs were filled in with Klenow polymerase, linked with Bst XI adapters, digested with Bst XI, and ligated into the Bst XI site of the pRcCMV vector (Invitrogen). The orientation of the insert in the expression vector was determined by restriction analysis with enzymes cutting the α7 subunit cDNA at asymmetrical positions. was determined by restriction analysis with enzymes cutting the α7 subunit cDNA at asymmetrical positions.

Expression of α7 nAChR in *Xenopus laevis* Oocytes and Measurement of Functional Characteristics The preparation of *Xenopus laevis* oocytes, injection with receptor RNA or DNA, and measurement of α7 nAChR responses using two-electrode voltage-clamp followed procedures described previously for the wild-type human α7 nAChR (Briggs et al. (1995), supra) except that atropine was not routinely present in the bathing solution. Oocytes were maintained at 17–18° C. in normal Barth's solution (90 mM NaCl, 1 mM KCl, 0.66 mM NaNO$_3$, 0.74 mM CaCl$_2$, 0.82 mM MgCl$_2$, 2.4 mM NaHCO$_3$, 2.5 mM sodium pyruvate, and 10 mM Na N-(2-hydroxyethyl)piperazine-N'-(2-ethanesulfonic acid) ("HEPES") buffer, final pH 7.55) containing 100 μg/ml gentamicin. Responses were measured at a holding potential of −60 mV in modified Barth's solution containing 10 mM BaCl$_2$ and lacking CaCl$_2$ and MgCl$_2$. However, in some experiments (FIG. 6) the cell potential was intentionally varied in order to determine the response current-voltage relationship and OR2 plus atropine (82.5 mM NaCl, 2.5 mM KCl, 2.5 mM CaCl$_2$, 1 mM MgCl$_2$, 5 mM Na-HEPES (pH 7.4) and 0.5 μM atropine sulfate) was used to replicate conditions used by Galzi et al. (1992), supra, to study chick α7 nAChR. Agonist was applied briefly using a computer-controlled solenoid valve and a push/pull applicator positioned to within 200–400 μm from the oocyte. Responses were recorded by computer in synchrony with agonist application. Antagonists were included with agonist in the push/pull applicator and were applied to the bath by superfusion for at least 3 minutes before application of agonist. Responses were quantified by measuring the peak amplitude.

Human α7V274T responses, unlike human (α7WT responses, tended to increase significantly during the experiments. Therefore, experimental trials were bracketed, before and after, by control applications of 10 μM ACh in the same oocyte. All responses were normalized to the ACh responses in order to account for changes in sensitivity within the experiment and for variability in receptor expression among oocytes.

EXAMPLE 1

Preparation of Human α7V274T cDNA

To generate the variant α7V274T in an expression vector, the wild-type of 7 subunit gene was digested with EcoR V and Kpn I restriction enzymes and the digested segment was replaced with a mutant PCR product by ligation using the procedures described below.

The strategy, diagrammed in FIG. 1, used two PCR steps followed by digesting with restriction enzymes to produce a mutated fragment of the wild-type α7 subunit cDNA and subcloning the mutated fragment into the wild-type human α7 cDNA. In the first step (A), two DNA fragments carrying the desired mutation were generated by PCR using appropriate primers. The mutated nucleotide was incorporated in the reverse primer (X-3') for the longer fragment and in the forward primer (Y-5') for the shorter fragment. The two external primers (X-5' and Y-3') were chosen so that the final PCR product would contain EcoRV and KpnI restriction sites.

The longer 5' fragment (X-5') was generated using the forward external primer 5'-GTTTGGGTCCTGGTCTTACG-3' (SEQ ID NO: 3) and the reverse internal primer (X-3') 5'-GCAGCATGAAGGTGGTAAGAGAG-3' (X-3') (SEQ ID NO: 4) bearing the mutation. The shorter 3' fragment was generated using the forward internal primer (Y-5') 5'-CTCTCTTACCACCTTCATGCTGC-3' (SEQ ID NO: 5), also bearing the mutation, and the reverse external primer (Y-3') 5'-GTACTGCAGCACGATCACCG-3' (SEQ ID NO: 6). The conditions for PCR consisted of 100 ng input α7 DNA, 2×Pfu buffer, 100 ng of each primer pair and 0.625 U Pfu enzyme (Stratagene, La Jolla, Calif.). Reactions were carried out in a Perkin-Elmer 9600 for 20 cycles at 95° C. for 24 seconds, 60° C. for 22 seconds then 72° C. for 78 seconds.

In the second PCR step (B), these two fragments were reassembled using the external primers. The sequence was reamplified and a longer DNA fragment bearing the desired mutation was generated.

In the next step (C), the product of step (B) was digested with KpnI and EcoRV, gel-purified, and ligated into the wild-type human α7 cDNA previously digested with KpnI and EcoRV. Dideoxy sequencing of the final cDNA showed the presence of the desired mutation and that no other mutation had been introduced during the PCR process.

FIGS. 2A–2C shows the nucleotide sequence (SEQ ID NO: 1) of the human α7V274T cDNA mutant. The amino acid sequence of the human α7V274T variant (SEQ ID NO: 2) also is shown in FIGS. 2A–2C.

EXAMPLE 2

Figure 3B:
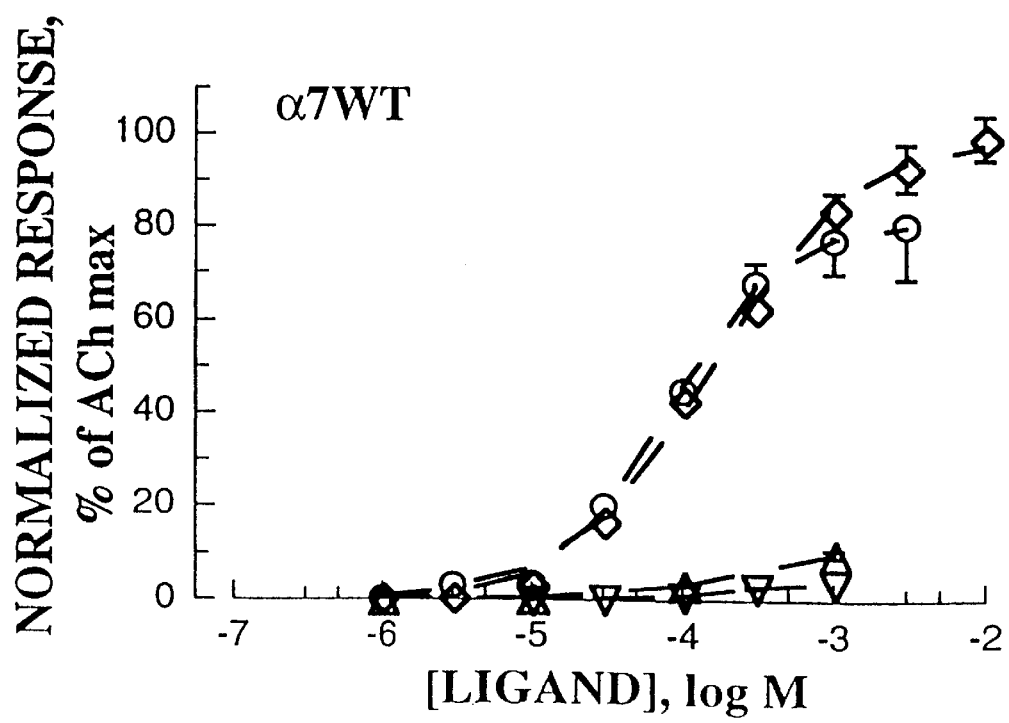

Concentration-Response Relationships for Agonists in Human αt7V274T and Wild-Type nAChR Responses to various agonist concentrations were measured using human α7V274T nAChR subunits expressed from the DNA prepared in Example 1 that was injected into *Xenopus laevis* oocytes as described above. Responses of human α7 subunit wild type nAChR were measured as described by Briggs et al. (1995) supra. The responses were measured at peak amplitude and were normalized to the response to ACh. Data points (FIG. 3) show the mean ±s.e.m. of the normalized responses (n=4 to 10 for ACh, n=3 to 4 for (−)-nicotine n=3 to 5 for GTS-21, and n=2 to 5 for ABT-089). The curves depicted in FIG. 3 show the Hill equation fitted to the data (Sigmaplot software, Jandel Scientific, San Rafael, Calif., U.S.A.) with the exception of the small responses to GTS-21 and ABT-089 at the α7 wild-type. At the human α7 wild type nAChR, ACh and (−)-nicotine had $EC_{50}$ values of 156±20 μM and 83±10 μM, respectively, and Hill coefficients of 0.94±0.09 and 1.2±0.2, respectively. GTS-21 and ABT-089 were partial agonists whose $EC_{50}$ values could not be estimated because the responses were so weak. There was a clear shift in potency and efficacy at the human α7V274T nAChR. At the human α7V274T nAChR, ACh and (−)-nicotine were two orders of magnitude more potent, with $EC_{50}$ values of 1.02±0.04 μM and 0.94±0.12 1 μM, respectively, and Hill coefficients of 1.8±0.2 and 1.3±0.2, respectively. More remarkably, GTS-21 was a full agonist at the human α7V274T nAChR with an $EC_{50}$ value of 4.3±0.3 μM and a Hill coefficient of 1.5±0.1, in stark contrast to its weak partial agonist effect at the human α7 wild type nAChR. ABT-089 also was more potent and efficacious at the human α7V274T nAChR, with an $EC_{50}$ value of 28±3 μM and a Hill coefficient of 2.3±0.4, but it was a partial agonist with an efficacy of 40±1%. These results with the human nAChR subunits correlate with the 180-fold increase in ACh potency observed with chick α7V251T compared to chick α7 wild type nAChR (Galzi et al. (1992), supra). However, this is the first demonstration that the potency of (−)-nicotine also is shifted, and the first demonstration that the potency and efficacy of a partial agonists are shifted in this variant.

EXAMPLE 3

Figure 4:
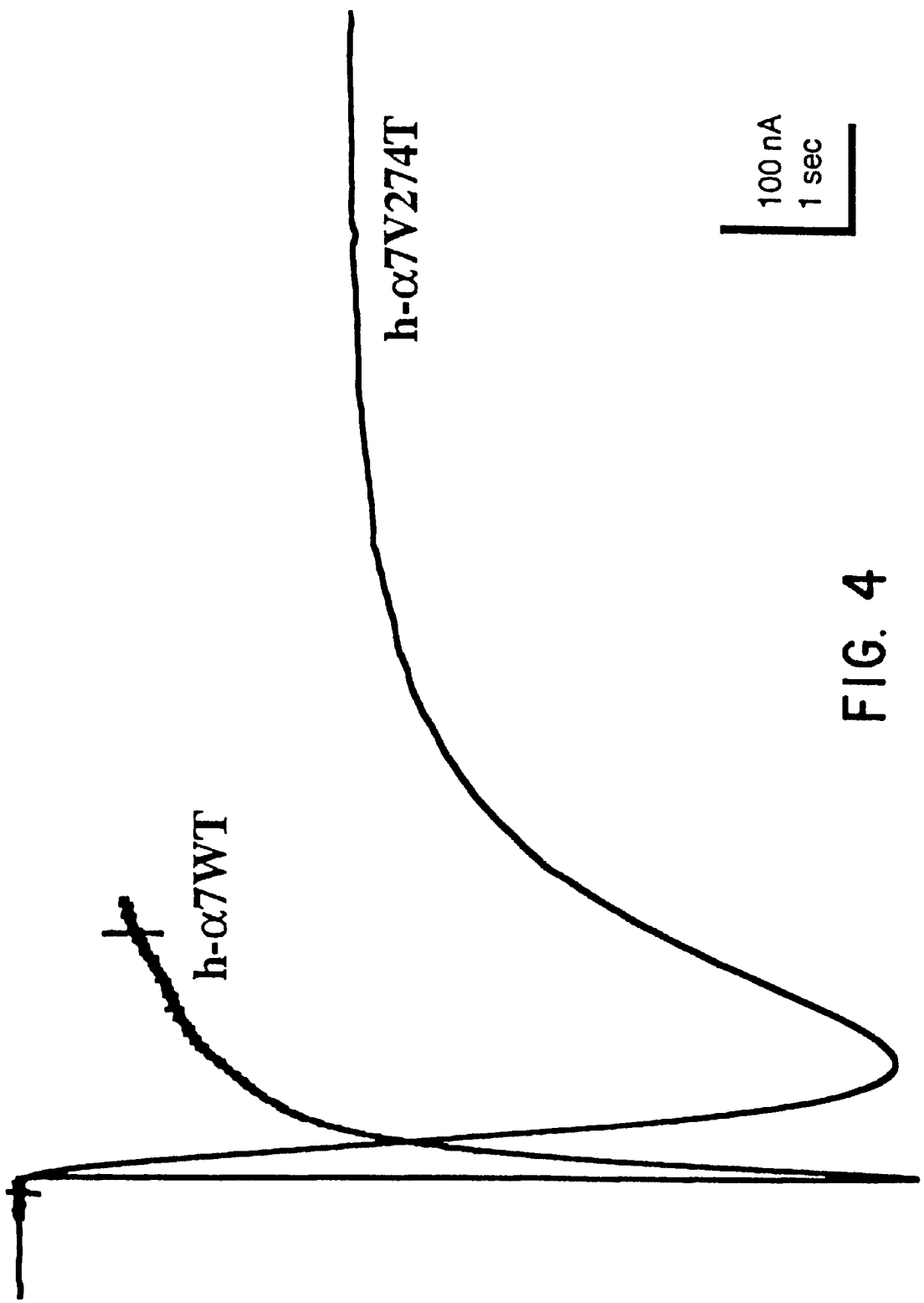
FIG. 4 graphically depicts the activation by ACh and decay rate of the human α7V274T response compared to that of the human α7 wild-type nAChR.

Activation and Decay Rate of Human α7V274T Compared to Wild-Type Human α7WT nAChR Human α7V274T and human α7 wild-type responses to $EC_{50}$ concentrations of ACh (1 μM and 200 μM, respectively) were matched for similar amplitude and are shown synchronized to the beginning of ACh application and adjusted for equivalent baseline holding current (see FIG. 4). ACh was applied to human α7V274T for 10 sec and to human α7 wild-type for 2.5 sec. Brief spike-like tics near the beginning and end of the human α7 wild-type trace are electrical artifacts marking the opening and closing of the agonist-application valve.

Human α7V274T responses activated and decayed slowly compared to the human α7 wild-type responses. Similarly, the analogous chick mutant nAChR activated and decayed more slowly in response to ACh (Galzi et al. (1992), supra.

EXAMPLE 4

Evaluation of nAChR Antagonists for Agonist Activity at the Human α7V274T nAChR nAChR antagonists such as dihydro-β-erythroidine (DHβE), d-tubocurarine and hexamethonium, have been found to activate responses at chick α7 TM-2 nAChR variants when these compounds were applied as agonists (Bertrand et al. (1992), supra). This, together with data from single-channel recording, has suggested (a) that the variant nAChRs conduct in the receptor-desensitized state and (b) that wild-type nAChR antagonists act by stabilizing the desensitized state (Bertrand et al. (1995), supra).

At the human of α7V274T nAChR, DHβE (10 μM) also activated agonist-like inward current responses (see FIG. 5). However, these responses were small, ranging from 2.8% to 6.9% of the response to 10 μM ACh (Table 1) unlike the homologous chick α7V251T nAChR where 10 μM DHβE elicited a response 66% as large as the ACh response (Bertrand et al. (1993), *Proc. Natl. Acad. Sci (U.S.A.)* 90: 6971–6975).

TABLE 1

Effects of Cholinergic Antagonists at the Human α7V274T Mutant and α7 Wiid-type nAChR

| nAChR | Ligand (μM) | % Activation[‡] 10 μM ACh | % Inhibition[§] 1 μM ACh | % Inhibition[§] 10 μM ACh |
|---|---|---|---|---|
| α7V274T | DHβE (10) | 4 ± 1 (4)* | 69 ± 5 (4)† | 52 ± 6 (4) (4)† |
|  | d-TC (1) | −2 ± 1 (4) | 99 ± 1 (4)† | 97 ± 3 (3)† |
|  | MLA (0.01) | −4 ± 2 (7)* | 103 ± 1 (4)† | 95 ± 3 (7)† |
|  | MEC (10) | −1.9 ± 0.2 (4)† | 101 ± 1 (4)† | 53 ± 2 (4)† |
|  | ATROP (2) | 0.1 ± 0.1 (4) | 28 ± 7 (5)* | 13 ± 5 (6)† |
|  |  | % of 10 mM ACh | % of 200 μM ACh | % of 10 mM ACh |
| α7WT | DHβE (10) | −0.2 ± 0.1 (5) | 41 ± 10 (4)* | 23 ± 2 (4)† |
|  | d-TC (1) | −0.1 ± 0.1 (5) | 28 ± 2 (4)† | 25 ± 3 (4)† |
|  | MLA (0.01) | −0.2 ± 0.4 (3) | 100 ± 0.5 (4) | 99 ± 0.4 (4)† |
|  | MEC (10) | −0.3 ± 0.2 (3) | 82 ± 1 (3)† | 85 ± 3 (3)† |
|  | ATROP (2) | 0.2 ± 0.5 (3) | 4 ± 3 (3) | 12 ± 3 (3)* |

Abbreviations: DHβE (dihydro-β-erythroidine); d-TC (d-tubocurarine); MLA (methyllycaconitine); MEC (mecamylamine); ATROP (atropine).
*$p < 0.05$ compared to 0 (Student's two-tailed t-test)
†$p < 0.005$ compared to 0 (Student's two-tailed t-test)
‡compared to activation by 10 μM
§% inhibition of the response to ACh Furthermore, at human α7V274T this was not a general property of nAChR antagonists. Both the α7-selective antagonist methyllycaconitine (MLA; 10 nM) and the non-selective nAChR antagonist mecamylamine (MEC; 10 μM) elicited the opposite effect, small inverse agonist-like outward currents ranging in amplitude from 0.9% to 12.4% of the maximal inward current response to ACh, as shown in FIG. 5 and Table 1. The traces shown in FIG. 5, all from a single oocyte, compare responses to MEC (10 μM), MLA (10 nM), DHβE (10 μM) and bathing solution (0-agonist control) applied for 20 sec each. The small 0-agonist control responses were measured in each human α7V274T oocyte and subtracted from agonist responses when data were tabulated. Calibration lines in FIG. 5 represent 10 nA and 2 sec for all traces.

d-Tubocurarine (d-TC; 1 μM) also did not elicit agonist-like inward currents, but did elicit small outward currents (3–5% of the maximal inward current response to ACh) in two of four human α7V274T oocytes. The outward current responses may be due to stabilization of the resting (closed) state or to channel blockade of spontaneously open nAChR. At the human α7 wild-type nAChR under similar conditions, neither DHβE (10 μM), MLA (10 nM), MEC (10 μM) nor d-TC (1 μM) elicited any significant inward or outward current response (Table 1). The muscarinic antagonist atropine (2 μM) alone had little effect at either nAChR.

EXAMPLE 5

Evaluation of nAChR Antagonists for Agonist Activity at the Human α7V274T nAChR

The above compounds also were evaluated as antagonists of the response to ACh at both human α7V274T and human α7 wild-type nAChRs. For each nAChR, two concentrations of ACh were used: one near the $EC_{50}$ value (1 μM for α7V274T and 200 μM for α7 wild-type) and one near the maximal response level (10 μM for α7V274T and 10 mM for α7 wild-type). Data are shown in Table 1. DHβE (10 μM), d-TC (1 μM), MLA (10 nM), and MEC (10 μM) acted as antagonists at both nAChRs. The α7 selective antagonist MLA was particularly potent, as expected, blocking human α7V274T as well as human α7 wild-type at a concentration of 10 nM. Interestingly, MEC (10 μM), DHβE (10 μM) and d-TC (1 μM) each appeared to inhibit human α7V274T more than human α7 wild-type. Atropine (2 μM) inhibited the human α7V274T response to 1 μM ACh by 28%, but had little effect on the human α7 wild-type response to 200 μM ACh. Some oocytes have endogenous muscarinic receptors activated by low-micromolar concentrations of ACh (Kusano et al. (1982) *J. Physiol.* (London) 328:143–170; Davidson et al. (1991) *FEBS Lett.* 284:252–256; and Dascal et al. (1980) *Life Sci.* 27:1423–1428). However, this does not appear to explain the effect of atropine on human α7V274T because the nAChR antagonist MEC (10 μM) completely blocked the response to 1 μM ACh in three of the five h-α7V274T oocytes inhibited by atropine (the other two were not exposed to MEC).

DHβE (10 μM) inhibited maximal ACh responses less strongly than it inhibited $EC_{50}$ ACh responses at both human α7V274T and human α7 wild-type (see Table 1). MEC (10 μM) also inhibited the maximal ACh response less strongly than the EC ACh response at the human α7V274T nAChR, but not at the human α7 wild-type nAChR where MEC inhibited both concentrations of ACh similarly. The lesser inhibitions at the higher concentrations of ACh may reflect competitive antagonist-agonist interactions.

Thus, the human variant α7V274T nAChR is similar to the analogous chick α7V251T nAChR in its increased sensitivity to agonist activation and apparent slower rate of activation and desensitization. The receptors differ, however, in that DHβE (10 μM) activated the human β7V274T inward current only weakly, compared to a 66% agonist-like effect at chick α7V251T, and in that d-TC did not activate inward currents at the h-α7V274T compared to the full response at chick α7L247T nAChR (Galzi et al. (1992), supra; Bertrand et al. (1993), supra). Thus, there is a difference in the effects of these sequence modifications on α7 nAChR function which difference is unexpected in view of the information known regarding chick α7V274T.

EXAMPLE 6

Human α7V274T Rectification

The current versus voltage relationship of human α7V274T variant nAChR responses to 10 μM ACh was measured in oocytes under two-electrode voltage clamp as described by Briggs et al. (1995) *Neuropharmacol.* 34:583–590. This was done under two conditions: (a) four oocytes in modified Barth's solution containing $Ba^{2+}$ to prevent secondary activation of $Ca^{2+}$-dependent $Cl^-$ currents (90 mM NaCl, 1 mM KCl, 0.66 mM $NaNO_3$, 10 mM $BaCl_2$, 2.5 mM sodium pyruvate, and 10 mM Na-HEPES buffer, pH 7.55), and (b) three oocytes in OR2 solution made to replicate that used by Galzi et al. (1992) supra, in their study of chick α7 variants (82.5 mM NaCl, 2.5 mM KCl, 2.5 mM CaCl$_2$, 1 mM MgCl$_2$, 0.5 μM atropine, and 5 mM Na-HEPES buffer, pH 7.4). Under both conditions, clear inward rectification of the ACh response was observed in that there was little current response at cell potentials above 0 mV compared to the current response at negative cell potentials. Similarly, human α7 wild-type nAChR (Briggs et al. (1995), supra) and chick α7 wild-type nAChR (Galzi et al. (1992), supra) show inward rectification, but the chick α7V251T variant did not show such rectification (Galzi et al. (1992), supra).

EXAMPLE 7

Expression Studies in Mammalian Cell Lines

Figure 7A:
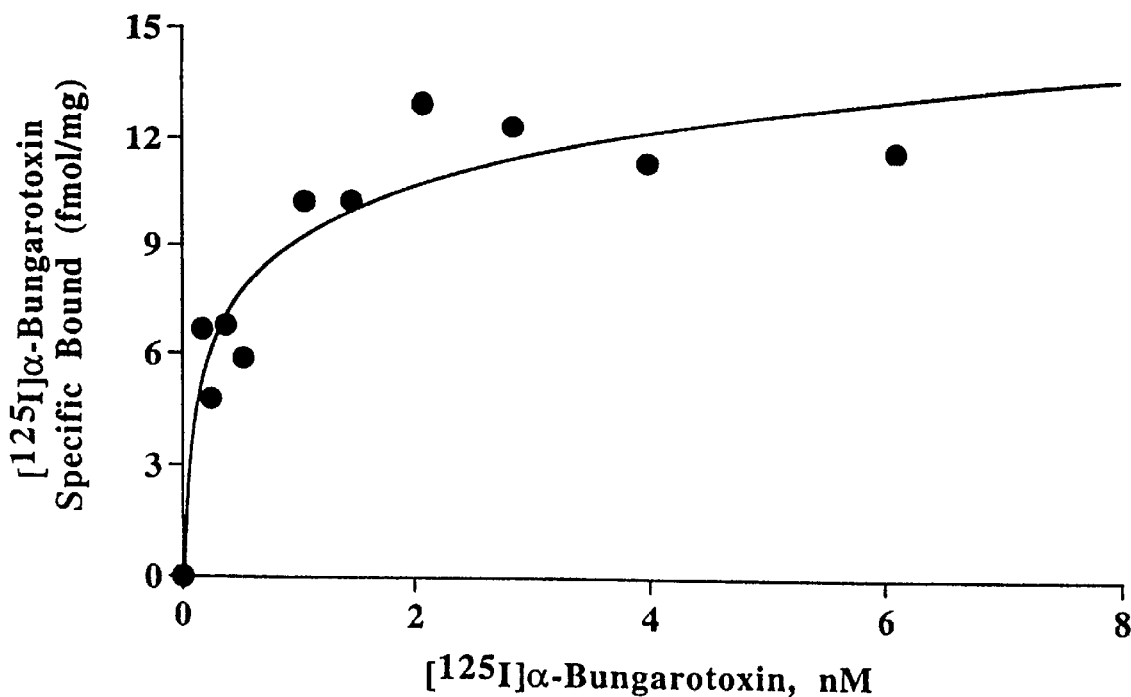
FIG. 7 graphically depicts the specific binding of [$^{125}$I] α-Bungarotoxin, an α7 nAChR-selective ligand, to an HEK-293 clone transfected with variant human α7V274T.
Figure 7B:
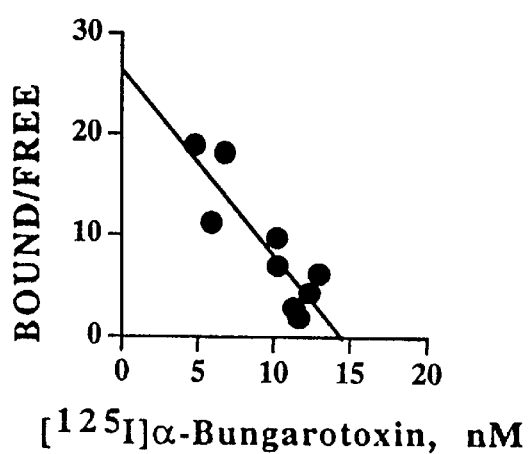

The human α7 wild-type and α7V274T mutant nAChR were transfected into the human embryonic kidney cell line, HEK-293 using the eukaryotic expression vector, pRc/CMV (Invitrogen, San Diego, Calif.) which contains the promoter sequences from the human cytomegalovirus for high level constitutive expression and contains the neomycin resistance gene for selection of geneticin-resistant stable cell lines. The cDNAs were transfected using lipofectamine (GIBCO) as described in (Gopalakrishnan et al. (1995) Eur. J. Pharmacol. (Mol. Pharm.) 290:237–246). Using this approach, stable cell lines expressing the human α7 wild-type nAChR have been generated, exhibiting clear [$^{125}$I]α-bungarotoxin binding, acetylcholine-evoked current and Ca$^{2+}$ influx responses (Gopalakrishnan et al. (1995), supra; Delbono et al. (1996) J. Pharmacol. Exp. Ther. (in press)). Additionally, initial data depicted in FIG. 7 demonstrates the feasibility of transfection of the α7 variant into mammalian cells.

The human α7V274T variant bears homology to the C. elegans deg-3 (u662) spontaneous mutation which appears to be cytotoxic through a mechanism that is inhibited by nicotinic antagonists (Treinin and Chalfie (1995) Neuron 14: 871–877). The human α7V274T variant nAChR response is more prolonged than wild-type responses (FIG. 4) but, like chick α7V251T variant nAChR, probably has high Ca$^{2+}$ permeability so that activation of the receptor may, under some conditions, lead to excessive Ca$^{2+}$ influx and thereby cell death. Further, there is some evidence that the human α7V274T variant nAChR may be prone to prolonged spontaneous opening because oocytes that have expressed α7V274T for 3 days or longer were 10–100 fold leakier electrically than were oocytes expressing human α7 wild-type nAChR. Thus, human α7V274T and related variant nAChR may be cytotoxic in the presence and even in the absence of agonist. Spontaneous expression of such a variant could interfere with normal α7 nAChR function, induce premature cell death, or interfere with synapse formation. Such effects could underlie some forms of neurodegenerative diseases or other disorders involving derangement of cholinergic function; for example, cognitive, immune and affective disorders.

Cytotoxicity clearly could limit the ability of cells to express the α7V274T variant at high levels. To circumvent this, transfected cells are grown in the presence of a reversible nicotinic antagonist or channel blocker, such as methyllycaconitine or mecamylamine. Such substances would prevent cytotoxicity by blocking the receptor or channel, but could be removed shortly before using the cells in further experiments.

Alternatively, for example, the human α7 wild type or variant is transfected using an inducible expression system such that expression of the α7 subunit is repressed until an inducer is added. The potential advantage of such an inducible system is that it can eliminate the cytotoxic effects of the expressed protein, for example the human α7V274T variant, that is observed when a constitutive expression system such as the pRcCMV is employed.

One of the expression vectors that is used is the Lac-Switch system (Stratagene) that uses the elements of lactose operon to control gene expression. With the LacSwitch system, basal expression is very low in the repressed state and once stably transfected in cell lines, this system permits rapid induction within 4–8 hours in presence of the inducing agent, IPTG. The system employs a eukaryotic Lac-repressor-expressing vector (p3'SS) and a eukaryotic lac-operator containing vector (pOPRSVI-CAT) into which the α7 subunit construct will be inserted by cloning. Antibiotic selection is attained via the hygromycin-resistance gene in p3'SS and via the neomycin-resistance gene in pOPRSVI-CAT vector. After transfection of HEK-293 or other cells, the selection of stable cell lines is achieved by the presence of both hygromycin and geneticin. Once stable cell lines are isolated, expression of the α7 subunit will be caused by the addition of the inducing agent, IPTG. In the absence of IPTG, transcription is blocked by the binding of the Lac repressor protein to the operator in pOPRSVI-CAT vector. IPTG decreases the binding affinity of the Lac repressor protein to the operator thereby triggering transcription and expression of the inserted α7 subunit gene. The choice of such a system permits the direct evaluation of the role of the mutant α7 nAChR in mediating cell death in vitro.

In Vitro Assessment of Cytotoxicity in Mammalian Cell Lines

To determine whether the human α7V274T variant mediates cytotoxicity, cell damage can be assessed following transient expression of the cDNA in HEK-293 cells by a number of methods, for example: (i) staining the cells with Trypan blue (4%) for 5 minutes and assessing the ability of viable cells to exclude the dye; (ii) measuring the levels of the cytosolic enzyme lactate dehydrogenase (LDH) released into the medium, as an index of cell lysis (e.g., Donnelly-Roberts et al. (1996) Brain Res. 719: 36–44); (iii) uptake of neutral red dye or uptake and conversion of the tetrazolium MTT as an index of viability (e.g., Little et al. (1996) Br. J. Dermatol. 134: 199–207; D'Souza et al. (1996) J. Neurosci. Res. 43: 289–298; Malcolm et al. (1996) J. Neurochem. 66: 2350–2360); (iv) uptake and binding of propidium iodide to nucleic acids (e.g., Wrobel et al. (1996) J. Immunol. Methods 189: 243–249) or other techniques that are sensitive to a loss of plasma membrane integrity or cellular metabolic function. Additional techniques may be used to assess changes in nucleotide incorporation, DNA structure or integrity (e.g., Alison and Sarraf (1995) Hum. Exp. Toxicol. 14: 234–247; Didier et al. (1996) J. Neurosci. 16: 2238–2250). These techniques are known to those of ordinary skill in the art. These studies are carried out in nontransfected or mocktransfected cells (controls), cells that are transfected with human α7 wild-type, and cells that are transfected with human α7V274T variant. Confirmation that human α7V274T variant expression leads to cytotoxicity would suggest a role in triggering neurodegenerative processes in vivo.

Diagnostic Application

The presence of the α7V274T variant in humans could be determined in a non-invasive manner, for example using the polymerase chain reaction (PCR) and genomic DNA isolated from blood samples following standard methodology. Alternatively, if RNA is isolated, then reverse transcriptase-PCR ("RT-PCR") can be utilized to detect the α7 variant. The PCR reaction, for example, could use 100 ng of the DNA in a standard 50 μl PCR reaction with the appropriate synthetic primers. For example, the external primers used in the synthesis of the α7 variant (X-5' and Y-3') would allow one to amplify the region of interest. The primers would be chosen to generate a distinct size fragment encompassing the sequence transmembrane segment 2, in which the V274T substitution takes place. Following amplification, the nucleotide sequence of the message is determined. The presence of the variant can be an indication of cellular disease, such as, neurodegeneration, or other forms of cytotoxicity.

Thus, a method of detecting target polynucleotides of human variant α7 subunit in a test sample comprises (a) contacting a target polynucleotide of human variant α7 subunit with at least one human variant α7 subunit-specific polynucleotide (probe) or complement thereof; and (b) detecting the presence of the target polynucleotide and probe complex in the test sample. Another method for detecting cDNA of human variant α7 subunit mRNA in a test sample comprises (a) performing reverse transcription in order to produce cDNA; (b) amplifying the cDNA obtained from step (a); and (c) detecting the presence of the human variant α7 subunit in the test sample. Alternatively, sampled DNA or cDNA prepared from RNA by RT-PCR, can be amplified using appropriate primers (for example, X-5' and Y-3') to allow detection of the variant by nucleotide sequence analysis. The detection step (c) comprises utilizing a detectable moiety capable of generating a measurable signal.

A purified polynucleotide or fragment thereof derived from human variant α7 subunit capable of selectively hybridizing to the nucleic acid of human variant α7 subunit can be utilized in these methods, wherein said polynucleotide is SEQUENCE ID NO: 1 or a fragment thereof. The purified polynucleotide can be produced by recombinant techniques.

A polypeptide encoded by human variant α7 subunit also is useful for diagnostic applications. The polypeptide is derived from SEQUENCE ID NO: 2 or fragments thereof. Further, the polypeptide can be produced by recombinant or synthetic techniques known in the art.

A monoclonal antibody which specifically binds to human variant α7 subunit also can be utilized in these methods. The human variant α7 subunit comprises an amino acid sequence SEQUENCE ID NO: 3 or fragments thereof.

A method for detecting human variant α7 subunit in a test sample can comprise (a) contacting said test sample with an antibody or fragment thereof which specifically binds to human variant α7 subunit for a time and under conditions sufficient for the formation of resultant complexes; and (b) detecting said resultant complexes containing said antibody, wherein said antibody specifically binds to human variant α7 subunit SEQUENCE ID NO: 2 or fragments thereof.

Treatment Application

Spontaneous mutation of human α7 valine-274 to threonine and related mutation could result in or hasten death of those cells expressing the protein. At least two types of treatment could be undertaken: (i) pharmacoogical intervention, for example, administration of a selective α7 antagonist such as methyllycaconitine or another compound with improved blood-brain barrier penetration; or, (ii) antisense oligonucleotide therapy to block the synthesis of the protein (e.g., see Albert and Morris (1994) Antisense knockouts: molecular scalpels for the dissection of signal transduction. *Trends in Pharmacological Sciences* 15: 250–254); or (iii) as a reagent to kill cells such as, cancer cells. For example, the antisense oligonucleotide may be used. Thus, this oligo or others would block synthesis of any α7 subunit protein, including wild type, but still would be of use where the variant and not the wild type is expressed, or where knockout of the wild-type is less detrimental than continued expression of the variant. The efficacy of this anti-sense would be demonstrated in vitro and farther, the antisense would be valuable as a research tool to evaluate α7 subunit function. both of which methods are based on binding of a polynucleotide to DNA or RNA. For example, the 5' coding portion of the polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription thereby preventing transcription and the production of the human variant α7 subunit polypeptide. The antisense RNA oligonucleotide hybridizes to the mRNA in vivo and blocks translation of an mRNA molecule into the human variant α7 subunit polypeptide. Antisense oligonucleotides act with greater efficacy when modified to contain artificial internucleotide linkages which render the molecule resistant to nucleolytic cleavage. Such artificial internucleotide linkages include but are not limited to methylphospnate, phosphorothiolate and phosphoroamydate internucleotide linkages.

Research and Drug Discovery Application

Antisense oligonucleotides also would be of value in determining α7 wild-type and V274T functions, and mechanisms of cytotoxicity in general. For example, one method of evaluating the contribution of α7V274T to cytotoxicity, cytoprotection, or other cellular processes would be to determine whether specific blockade of its synthesis blocks such processes. This differs in approach from the use of a receptor antagonist, which may or may not block all effects of the protein. Additionally, in drug discovery this approach could be useful in evaluating whether the effect of the drug is mediated by the α7V274T variant. A similar approach could be used to evaluate the contribution of other variants or the wild-type subunit itself. In control experiments, the corresponding α7 sense and missense oligonucleotides 5'-CGAGCCCATGAGGTGTAGCC (SEQUENCE ID NO: 7) and 5'-CCAGGCATTCGGAGCTTGCC (SEQUENCE ID NO: 8), respectively, are used. The missense oligonucleotide is a randomized sequence maintaining the proportion of GC content in the antisense oligonucleotide, and did not match known sequences in the GenBank® database.

Thus, polynucleotides that encode novel subunit and their antisense variants of the human α7 nAChR can be used in a variety of ways as detailed herein. Although preferred embodiments of the subject invention have been described in some detail, it is understood that obvious variations can be made without departing from the spirit and the scope of the invention as defined by the appended claims.

We claim:

1. A purified polynucleotide encoding a variant of a wild-type human α7 subunit, wherein the polynucleotide encodes a polypeptide having an amino acid substitution at position valine-274 of the wild-type human α7 subunit, said variant sequence as disclosed in SEQ ID NO 2.

2. The polynucleotide of claim 1, wherein the polynucleotide is a polydeoxyribonucleotide (DNA).

3. The polynucleotide of claim 1, wherein the polynucleotide is a polyribonucleotide (RNA).

4. A host cell comprising the polynucleotide of claim 1.

5. The host cell of claim 4, wherein said cell is selected from the group consisting of a bacterial cell, a mammalian cell, a yeast cell, an amphibian cell and a starfish cell.

6. The host cell of claim 5, wherein the cell is an amphibian cell.

7. The host cell of claim 5, wherein the cell is a mammalian cell.

8. An expression vector comprising the polynucleotide of claim 1 operably linked to control sequences that direct the transcription of the polynucleotide whereby said polynucleotide is expressed in a host cell.

9. The expression vector of claim 8, wherein the variant human α7 subunit is a human α7V274T subunit.

10. A host cell comprising the expression vector of claim 8.

11. The host cell of claim 10, wherein the cell is selected from the group consisting of a bacterial cell, a mammalian cell, a yeast cell and an amphibian cell.

12. The host cell of claim 11, wherein the cell is an amphibian cell.

13. The host cell of claim 11, wherein the cell is a mammalian cell.

14. A host cell comprising the expression vector of claim 9.

15. The host cell of claim 14, wherein the cell is selected from the group consisting of a bacterial cell, a mammalian cell, a yeast cell and an amphibian cell.

16. The host cell of claim 15, wherein the cell is an amphibian cell.

17. The host cell of claim 15, wherein the cell is a mammalian cell.

18. A method for producing a variant human of α7 receptor, comprising:
  (a) culturing the host cell of claim 10 under conditions that allow the production of the variant human α7 receptor; and
  (b) recovering the variant human α7 receptor.

19. A method for producing a variant human α7 receptor, comprising:
  (a) culturing the host cell of claim 14 under conditions that allow the production of the variant human α7 receptor; and
  (b) recovering the variant human α7 receptor.

20. The purified polynucleotide of claim 1 wherein said polynucleotide is produced by recombinant techniques.

* * * * *

SEQUENCE LISTING

<160> NUMBER OF SEQ ID NOS: 8

<210> SEQ ID NO 1
<211> LENGTH: 1590
<212> TYPE: DNA
<213> ORGANISM: homo sapien
<220> FEATURE:
<221> NAME/KEY: CDS
<222> LOCATION: (9)...(1514)

<400> SEQUENCE: 1

```
tcgagccc atg agg tgt agc ccc gga gga gtg tgg ctg gca ctg gca gca        50
         Met Arg Cys Ser Pro Gly Gly Val Trp Leu Ala Leu Ala Ala
         1               5                  10 tct ctc ctg cac gtg tcc ctg caa ggc gag ttc cag agg aag ctt tac         98
Ser Leu Leu His Val Ser Leu Gln Gly Glu Phe Gln Arg Lys Leu Tyr
 15              20                  25                  30 aag gag ctg gtc aag aac tac aat ccc ttg gag agg ccc gtg gcc aat        146
Lys Glu Leu Val Lys Asn Tyr Asn Pro Leu Glu Arg Pro Val Ala Asn
                 35                  40                  45 gac tcg caa cca ctc acc gtc tac ttc tcc ctg agc ctc ctg cag atc        194
Asp Ser Gln Pro Leu Thr Val Tyr Phe Ser Leu Ser Leu Leu Gln Ile
             50                  55                  60 atg gac gtg gat gag aag aac caa gtt tta acc acc aac att tgg ctg        242
Met Asp Val Asp Glu Lys Asn Gln Val Leu Thr Thr Asn Ile Trp Leu
         65                  70                  75 caa atg tct tgg aca gat cac tat tta cag tgg aat gtg tca gaa tat        290
Gln Met Ser Trp Thr Asp His Tyr Leu Gln Trp Asn Val Ser Glu Tyr
     80                  85                  90 cca ggg gtg aag act gtt cgt ttc cca gat ggc cag att tgg aaa cca        338
Pro Gly Val Lys Thr Val Arg Phe Pro Asp Gly Gln Ile Trp Lys Pro
 95                 100                 105                 110 gac att ctt ctc tat aac agt gct gat gag cgc ttt gac gcc aca ttc        386
Asp Ile Leu Leu Tyr Asn Ser Ala Asp Glu Arg Phe Asp Ala Thr Phe
                115                 120                 125 cac act aac gtg ttg gtg aat tct tct ggg cat tgc cag tac ctg cct        434
His Thr Asn Val Leu Val Asn Ser Ser Gly His Cys Gln Tyr Leu Pro
            130                 135                 140 cca ggc ata ttc aag agt tcc tgc tac atc gat gta cgc tgg ttt ccc        482
Pro Gly Ile Phe Lys Ser Ser Cys Tyr Ile Asp Val Arg Trp Phe Pro
        145                 150                 155 ttt gat gtg cag cac tgc aaa ctg aag ttt ggg tcc tgg tct tac gga        530
Phe Asp Val Gln His Cys Lys Leu Lys Phe Gly Ser Trp Ser Tyr Gly
    160                 165                 170 ggc tgg tcc ttg gat ctg cag atg cag gag gca gat atc agt ggc tat        578
Gly Trp Ser Leu Asp Leu Gln Met Gln Glu Ala Asp Ile Ser Gly Tyr
175                 180                 185                 190 atc ccc aat gga gaa tgg gac cta gtg gga atc ccc ggc aag agg agt        626
Ile Pro Asn Gly Glu Trp Asp Leu Val Gly Ile Pro Gly Lys Arg Ser
                195                 200                 205 gaa agg ttc tat gag tgc tgc aaa gag ccc tac ccc gat gtc acc ttc        674
Glu Arg Phe Tyr Glu Cys Cys Lys Glu Pro Tyr Pro Asp Val Thr Phe
            210                 215                 220 aca gtg acc atg cgc cgc agg aca ctc tac tat ggc ctc aac ctg ctg        722
Thr Val Thr Met Arg Arg Arg Thr Leu Tyr Tyr Gly Leu Asn Leu Leu
        225                 230                 235 atc ccc tgt gtg ctc atc tcc gcc ctc gcc ctg ctg gtg ttc ctg ctt        770
Ile Pro Cys Val Leu Ile Ser Ala Leu Ala Leu Leu Val Phe Leu Leu
    240                 245                 250
```

-continued

| | | |
|---|---|---|
| cct gca gat tcc ggg gag aag att tcc ctg ggg ata aca gtc tta ctc<br>Pro Ala Asp Ser Gly Glu Lys Ile Ser Leu Gly Ile Thr Val Leu Leu<br>255                         260                        265                        270 | 818 |
| tct ctt acc acc ttc atg ctg ctc gtg gct gag atc atg ccc gca aca<br>Ser Leu Thr Thr Phe Met Leu Leu Val Ala Glu Ile Met Pro Ala Thr<br>                        275                        280                        285 | 866 |
| tcc gat tcg gta cca ttg ata gcc cag tac ttc gcc agc acc atg atc<br>Ser Asp Ser Val Pro Leu Ile Ala Gln Tyr Phe Ala Ser Thr Met Ile<br>                  290                        295                        300 | 914 |
| atc gtg ggc ctc tcg gtg gtg gtg acg gtg atc gtg ctg cag tac cac<br>Ile Val Gly Leu Ser Val Val Val Thr Val Ile Val Leu Gln Tyr His<br>              305                        310                        315 | 962 |
| cac cac gac ccc gac ggc ggc aag atg ccc aag tgg acc aga gtc atc<br>His His Asp Pro Asp Gly Gly Lys Met Pro Lys Trp Thr Arg Val Ile<br>320                        325                        330 | 1010 |
| ctt ctg aac tgg tgc gcg tgg ttc ctg cga atg aag agg ccc ggg gag<br>Leu Leu Asn Trp Cys Ala Trp Phe Leu Arg Met Lys Arg Pro Gly Glu<br>335                        340                        345                        350 | 1058 |
| gac aag gtg cgc ccg gcc tgc cag cac aag cag cgg cgc tgc agc ctg<br>Asp Lys Val Arg Pro Ala Cys Gln His Lys Gln Arg Arg Cys Ser Leu<br>                  355                        360                        365 | 1106 |
| gcc agt gtg gag atg agc gcc gtg gcg ccg ccg ccc gcc agc aac ggg<br>Ala Ser Val Glu Met Ser Ala Val Ala Pro Pro Pro Ala Ser Asn Gly<br>              370                        375                        380 | 1154 |
| aac ctg ctg tac atc ggc ttc cgc ggc ctg gac ggc gtg cac tgt gtc<br>Asn Leu Leu Tyr Ile Gly Phe Arg Gly Leu Asp Gly Val His Cys Val<br>385                        390                        395 | 1202 |
| ccg acc ccc gac tct ggg gta gtg tgt ggc cgc atg gcc tgc tcc ccc<br>Pro Thr Pro Asp Ser Gly Val Val Cys Gly Arg Met Ala Cys Ser Pro<br>             400                        405                        410 | 1250 |
| acg cac gat gag cac ctc ctg cac ggc ggg caa ccc ccc gag ggg gac<br>Thr His Asp Glu His Leu Leu His Gly Gly Gln Pro Pro Glu Gly Asp<br>415                        420                        425                        430 | 1298 |
| ccg gac ttg gcc aag atc ctg gag gag gtc cgc tac att gcc aac cgc<br>Pro Asp Leu Ala Lys Ile Leu Glu Glu Val Arg Tyr Ile Ala Asn Arg<br>                  435                        440                        445 | 1346 |
| ttc cgc tgc cag gac gaa agc gag gcg gtc tgc agc gag tgg aag ttc<br>Phe Arg Cys Gln Asp Glu Ser Glu Ala Val Cys Ser Glu Trp Lys Phe<br>              450                        455                        460 | 1394 |
| gcc gcc tgt gtg gtg gac cgc ctg tgc ctc atg gcc ttc tcg gtc ttc<br>Ala Ala Cys Val Val Asp Arg Leu Cys Leu Met Ala Phe Ser Val Phe<br>              465                        470                        475 | 1442 |
| acc atc atc tgc acc atc ggc atc ctg atg tcg gct ccc aac ttc gtg<br>Thr Ile Ile Cys Thr Ile Gly Ile Leu Met Ser Ala Pro Asn Phe Val<br>            480                        485                        490 | 1490 |
| gag gcc gtg tcc aaa gac ttt gcg taaccacgcc tggttctgta catgtggaaa<br>Glu Ala Val Ser Lys Asp Phe Ala<br>495                        500 | 1544 |
| actcacagat gggcaagcgc tttggcttgg cgagattcgg ccggaa | 1590 |

<210> SEQ ID NO 2
<211> LENGTH: 502
<212> TYPE: PRT
<213> ORGANISM: homo sapien

<400> SEQUENCE: 2

Met Arg Cys Ser Pro Gly Gly Val Trp Leu Ala Leu Ala Ala Ser Leu
 1               5                   10                  15

Leu His Val Ser Leu Gln Gly Glu Phe Gln Arg Lys Leu Tyr Lys Glu
               20                   25                   30

-continued

```
Leu Val Lys Asn Tyr Asn Pro Leu Glu Arg Pro Val Ala Asn Asp Ser
         35                  40                  45

Gln Pro Leu Thr Val Tyr Phe Ser Leu Ser Leu Gln Ile Met Asp
 50                  55                  60

Val Asp Glu Lys Asn Gln Val Leu Thr Thr Asn Ile Trp Leu Gln Met
 65                  70                  75                  80

Ser Trp Thr Asp His Tyr Leu Gln Trp Asn Val Ser Glu Tyr Pro Gly
                 85                  90                  95

Val Lys Thr Val Arg Phe Pro Asp Gly Gln Ile Trp Lys Pro Asp Ile
             100                 105                 110

Leu Leu Tyr Asn Ser Ala Asp Glu Arg Phe Asp Ala Thr Phe His Thr
             115                 120                 125

Asn Val Leu Val Asn Ser Ser Gly His Cys Gln Tyr Leu Pro Pro Gly
     130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                 165                 170                 175

Ser Leu Asp Leu Gln Met Gln Glu Ala Asp Ile Ser Gly Tyr Ile Pro
             180                 185                 190

Asn Gly Glu Trp Asp Leu Val Gly Ile Pro Gly Lys Arg Ser Glu Arg
         195                 200                 205

Phe Tyr Glu Cys Cys Lys Glu Pro Tyr Pro Asp Val Thr Phe Thr Val
     210                 215                 220

Thr Met Arg Arg Arg Thr Leu Tyr Tyr Gly Leu Asn Leu Leu Ile Pro
225                 230                 235                 240

Cys Val Leu Ile Ser Ala Leu Ala Leu Leu Val Phe Leu Leu Pro Ala
                 245                 250                 255

Asp Ser Gly Glu Lys Ile Ser Leu Gly Ile Thr Val Leu Leu Ser Leu
             260                 265                 270

Thr Thr Phe Met Leu Leu Val Ala Glu Ile Met Pro Ala Thr Ser Asp
         275                 280                 285

Ser Val Pro Leu Ile Ala Gln Tyr Phe Ala Ser Thr Met Ile Ile Val
     290                 295                 300

Gly Leu Ser Val Val Thr Val Ile Val Leu Gln Tyr His His His
305                 310                 315                 320

Asp Pro Asp Gly Gly Lys Met Pro Lys Trp Thr Arg Val Ile Leu Leu
                 325                 330                 335

Asn Trp Cys Ala Trp Phe Leu Arg Met Lys Arg Pro Gly Glu Asp Lys
             340                 345                 350

Val Arg Pro Ala Cys Gln His Lys Gln Arg Arg Cys Ser Leu Ala Ser
         355                 360                 365

Val Glu Met Ser Ala Val Ala Pro Pro Ala Ser Asn Gly Asn Leu
     370                 375                 380

Leu Tyr Ile Gly Phe Arg Gly Leu Asp Gly Val His Cys Val Pro Thr
385                 390                 395                 400

Pro Asp Ser Gly Val Val Cys Gly Arg Met Ala Cys Ser Pro Thr His
                 405                 410                 415

Asp Glu His Leu Leu His Gly Gly Gln Pro Pro Glu Gly Asp Pro Asp
             420                 425                 430

Leu Ala Lys Ile Leu Glu Glu Val Arg Tyr Ile Ala Asn Arg Phe Arg
         435                 440                 445
```

-continued

```
Cys Gln Asp Glu Ser Glu Ala Val Cys Ser Glu Trp Lys Phe Ala Ala
    450                 455                 460
Cys Val Val Asp Arg Leu Cys Leu Met Ala Phe Ser Val Phe Thr Ile
465                 470                 475                 480
Ile Cys Thr Ile Gly Ile Leu Met Ser Ala Pro Asn Phe Val Glu Ala
                485                 490                 495
Val Ser Lys Asp Phe Ala
            500
```

<210> SEQ ID NO 3
<211> LENGTH: 20
<212> TYPE: DNA
<213> ORGANISM: Homo Sapien

<400> SEQUENCE: 3
gtttgggtcc tggtcttacg                    20

<210> SEQ ID NO 4
<211> LENGTH: 23
<212> TYPE: DNA
<213> ORGANISM: Homo Sapien

<400> SEQUENCE: 4
gcagcatgaa ggtggtaaga gag                23

<210> SEQ ID NO 5
<211> LENGTH: 23
<212> TYPE: DNA
<213> ORGANISM: Homo Sapien

<400> SEQUENCE: 5
ctctcttacc accttcatgc tgc                23

<210> SEQ ID NO 6
<211> LENGTH: 20
<212> TYPE: DNA
<213> ORGANISM: Homo Sapien

<400> SEQUENCE: 6
gtactgcagc acgatcaccg                    20

<210> SEQ ID NO 7
<211> LENGTH: 20
<212> TYPE: DNA
<213> ORGANISM: Homo Sapein

<400> SEQUENCE: 7
cgagcccatg aggtgtagcc                    20

<210> SEQ ID NO 8
<211> LENGTH: 20
<212> TYPE: DNA
<213> ORGANISM: Homo Sapien

<400> SEQUENCE: 8
ccaggcattc ggagcttgcc                    20